US009238689B2

(12) United States Patent
Zierow et al.

(10) Patent No.: US 9,238,689 B2
(45) Date of Patent: Jan. 19, 2016

(54) ANTIBODIES THAT ARE CROSS-REACTIVE FOR MACROPHAGE MIGRATION INHIBITORY FACTOR (MIF) AND D-DOPACHROME TAUTOMERASE (D-DT)

(75) Inventors: Swen Zierow, Kundl (AU); Juergen Klattig, Peissenberg (DE)

(73) Assignee: Morpho Sys AG, Martinsried (DE)

(*) Notice: Subject to any disclaimer, the term of this patent is extended or adjusted under 35 U.S.C. 154(b) by 0 days.

(21) Appl. No.: 14/126,450

(22) PCT Filed: Jul. 13, 2012

(86) PCT No.: PCT/EP2012/063832
§ 371 (c)(1),
(2), (4) Date: Dec. 16, 2013

(87) PCT Pub. No.: WO2013/010955
PCT Pub. Date: Jan. 24, 2013

(65) Prior Publication Data
US 2014/0120115 A1    May 1, 2014

Related U.S. Application Data

(60) Provisional application No. 61/508,091, filed on Jul. 15, 2011.

(30) Foreign Application Priority Data

Jul. 15, 2011    (EP) ..................... 11174199

(51) Int. Cl.
*C07K 16/24* (2006.01)
*A61K 39/395* (2006.01)
*C07K 16/40* (2006.01)

(52) U.S. Cl.
CPC .............. *C07K 16/24* (2013.01); *C07K 16/40* (2013.01); *C07K 2317/33* (2013.01); *C07K 2317/76* (2013.01); *C07K 2317/92* (2013.01)

(58) Field of Classification Search
CPC ............... A61K 2039/505; A61K 39/3955; C07K 16/24; C07K 2316/96; C07K 2317/92; C07K 14/523; C07K 16/40; C07K 2317/76
See application file for complete search history.

(56) References Cited

U.S. PATENT DOCUMENTS

| RE43,497 E | 6/2012 | Brunner |
| 2003/0235584 A1 | 12/2003 | Kloetzer |
| 2005/0025767 A1 | 2/2005 | Nishihira |
| 2005/0202010 A1 | 9/2005 | Giroir |
| 2006/0034832 A1 | 2/2006 | Kimura |
| 2008/0305118 A1 | 12/2008 | Al-Abed |
| 2009/0220521 A1 | 9/2009 | Kerschbaumer |
| 2010/0260768 A1 | 10/2010 | Kerschbaumer |
| 2011/0044988 A1 | 2/2011 | Bernhagen |

FOREIGN PATENT DOCUMENTS

| WO | 9426307 | 11/1994 |
| WO | 1994026923 | 11/1994 |
| WO | 9817314 | 4/1998 |
| WO | 0138566 | 5/2001 |
| WO | 0236774 | 5/2002 |
| WO | 2002079517 | 10/2002 |
| WO | 2003060468 | 7/2003 |
| WO | 2005020919 | 3/2005 |
| WO | 2005082008 | 9/2005 |
| WO | 2005094329 | 10/2005 |
| WO | 2005094338 | 10/2005 |
| WO | 2006116688 | 11/2006 |
| WO | 2007042309 | 4/2007 |
| WO | 2008005528 | 7/2007 |
| WO | 2009086920 | 7/2009 |
| WO | 2009117706 | 9/2009 |
| WO | 2009117710 | 9/2009 |
| WO | 2009120186 | 10/2009 |
| WO | 2010015608 | 2/2010 |
| WO | 2010042548 | 4/2010 |
| WO | 2010056910 | 5/2010 |
| WO | 2010065491 | 6/2010 |
| WO | 2010017224 | 2/2011 |
| WO | 2011038149 | 3/2011 |
| WO | 2011146824 | 11/2011 |
| WO | 2012071525 | 5/2012 |
| WO | 2013023233 | 2/2013 |

OTHER PUBLICATIONS

PCT/EP2012/063998 International Search Report dated Oct. 12, 2012.
EP 11174199.7 extended European search report dted Dec. 13, 2011.
Xin Dan et al.: "The MIF Homologue D-Dopachrome Tautomerase Promotes COX-2 Expression through beta-Catenin-Dependend and —Independent Mechanisms", Molecular Caner Research, vol. 8, No. 12, Dec. 2010, pp. 1606-1609.
Hoi A.J. (2007) Inflammation & Allergy—Drug Targets, vol. 6, No. 3, 183-190.
David, J. (1966) Proc. Natl. Acad. Sci. U.S.A. 56: 72-77.
Bloom, B. R & Bennett, B. (1966) Science 153, 80-82.
Calandra, T. (2003) Nature Reviews Immunology vol. 03; 791-800.
Sun, H.W., (1996) Proc. Natl. Acad. Sci. U.S.A. 93: 5191-5196.
Bernhagen, J. (1993) Nature 365:756-759.
Calandra, T. (1994) J. Exp. Med. 179:1895-1902.
Lang L. (2003) J. Exp. Med. 197:1467-1476.
Bernhagen, J. (2007) Nature Medicine 13: 587-596.
Baugh, J.A. (2002) Genes Immun. 3: 170-176.
Hudson, J.D. (1999) J. Exp. Med. 190:1375-1382.
Sugimoto et al., Crystal Structure of Human D-Dopachrome Tautomerase, a Homologue of Macrophage Migration Inhibitory Factor, at 1.54A° C. Resolution, Biochemistry (1999) 38: 3268-3279.

*Primary Examiner* — Daniel C Gamett
(74) *Attorney, Agent, or Firm* — Paul F. Wiegel

(57) ABSTRACT

The present disclosure relates to antigen-binding moieties that specifically bind to MIF and D-DT and compositions and methods of use thereof.

34 Claims, 6 Drawing Sheets

FIGURE 1

```
MIF_HUMAN    PMFIVNTNVPRASVPDGFLSELTQQLAQATGKPPQYIAVHVVPDQLMAF
D-DT_HUMAN   PFLELDTNLPANRVPAGLEKRLCAAAASILGKPADRVNVTVRPGLAMAL
             *::  ::**:*    ** *: ..*    *.  ***.: :  * * *.  **:

MIF_HUMAN    GGSSEPCALCSLHSIGKIGGAQ-NRSYSKLLCGLLAERLRISPDRVYINY
D-DT_HUMAN   SGSTEPCAQLSISSIGVVGTAEDNRSHSAHFFEFLTKELALGQDRILIRF
             .**:****  *:  *** :* *: ***:*   :   :*::.*  :. **: *.:

MIF_HUMAN    YDMNAANVGWNN--STFA
D-DT_HUMAN   FPLESWQIGKIGTVMTFL
             :  ::: ::*   .    **
```

ANTIBODIES THAT ARE CROSS-REACTIVE FOR MACROPHAGE MIGRATION INHIBITORY FACTOR (MIF) AND D-DOPACHROME TAUTOMERASE (D-DT)

CROSS REFERENCE TO RELATED APPLICATIONS

This application claims the benefit of U.S. provisional application Ser. No. 61/508,091 filed Jul. 15, 2011, which is incorporated by reference in its entirety.

FIELD OF THE INVENTION

This disclosure generally relates to antibodies or fragments thereof which cross-react with Macrophage Migration Inhibitory Factor (MIF) and D-Dopachrome Tautomerase (D-DT). In particular, it relates to antibodies or fragments thereof that cross-react with MIF and D-DT and interfere with MIF-mediated and/or D-DT-mediated signal transduction. The disclosure further relates to therapeutics comprising MIF and D-DT cross-reactive antibodies and methods of treatment using compounds that share the ability to interact with MIF and D-DT.

BACKGROUND OF THE INVENTION

The human macrophage migration inhibitory factor (MIF, also known as GIF, GLIF, Glycosylation-inhibiting factor, L-dopachrome isomerase or L-dopachrome tautomerase) is described in David, J. (1966) *Proc. Natl. Acad. Sci. U.S.A.* 56: 72-77 and Bloom, B. R & Bennett, B. (1966) *Science* 153, 80-82 and was identified as a central regulator of innate immunity and inflammatory responses (Calandra, T. (2003) *Nature Reviews Immunology* Vol. 03; 791-800).

The MIF gene is located on chromosome 22 of the human genome and encodes a 115 amino acids long non-glycosylated protein of 12.5 kDa which forms a homotrimer (Sun, H. W., (1996) *Proc. Natl. Acad. Sci. U.S.A.* 93: 5191-5196).

MIF is constitutively expressed in virtually all cell types. During inflammation macrophages, T cells and the pituitary gland are the predominant sources of MIF (Bernhagen, J. (1993) *Nature* 365:756-759; Calandra, T. (1994) *J. Exp. Med.* 179:1895-1902). Secreted MIF interacts with its receptors CD74, CXCR2 and CXCR4 which are expressed e.g. on macrophages and T-cells and induces release of pro-inflammatory cytokines (e.g. TNFα, IL-1β, IL-6 IL-8, IFNγ, IL-2), cell invasion and cell migration (Leng L. (2003) *J. Exp. Med.* 197:1467-1476; Bernhagen, J. (2007) *Nature Medicine* 13: 587-596).

MIF as a pro-inflammatory mediator was identified to be involved and overexpressed in several inflammatory diseases and also polymorphisms of MIF were shown to correlate with the severity of autoinflammatory diseases (Hoi, A. J. (2007) *Inflammation & Allergy—Drug Targets,* 6: 183-190; Baugh, J. A. (2002) *Genes Immun.* 3: 170-176).

In addition, further studies describe that MIF negatively regulates p53-mediated apoptosis and cell arrest and thereby provide a link between MIF, cell growth and tumorigenesis (Calandra, T. (2003) *Nature Reviews Immunology* 03; 791-800; Hudson, J. D. (1999) *J. Exp. Med.* 190:1375-1382).

Upon identifying MIF as a key player not only in the pathogenesis of a range of immune-mediated inflammatory diseases but also in cancer and further indications, MIF became a promising therapeutic target to be antagonized with compounds like e.g. small molecules or monoclonal antibodies.

Antibodies specific for MIF are disclosed e.g. in WO1994/026307 (The Picower Institute For Medical Research), U.S. Ser. No. 08/471,705 which are all incorporated by reference in its entirety; WO1998/017314 (The Picower Institute For Medical Research), WO2001/038566 (Fraunhofer-Gesellschaft Zur Förderung Der Angewandten Forschung E.V.), U.S. Ser. No. 12/234,407 which are all incorporated by reference in its entirety; WO2002/036774 (Fraunhofer-Gesellschaft Zur Förderung Der Angewandten Forschung E.V.), WO2009/086920 (Baxter International Inc., Baxter Healthcare S.A., Dyax Corporation), U.S. Ser. Nos. 12/346,309 and 12/767,635 which are all incorporated by reference in its entirety; WO2009/117710 (Carolus Therapeutics Inc.), WO2009/117706 (Carolus Therapeutics Inc.), U.S. Ser. No. 12/918,968 which are all incorporated by reference in its entirety; WO2005/020919 (Cytokine Pharmasciences, Inc.), WO2005/094329 (Cytokine Pharmasciences, Inc.), U.S. Ser. No. 10/927,494 which are all incorporated by reference in its entirety; WO2005/094338A2 (North Shore-Long Island Jewish Research Institute), U.S. Ser. No. 10/594,641 which are all incorporated by reference in its entirety.

Notably, based on the finding that MIF is enzymatically active as a tautomerase and converts D-Dopachrome into 5,6-dihydroxyindole-2-carboxylic acid a homolog of MIF was identified which shares the tautomerase activity producing a similar but not identical product, 5,6-dihydroxyindole. The MIF homolog, which is called D-dopachrome tautomerase (D-DT), shows low sequence homology of 47% to MIF (FIG. 1). In 2008 it was shown that D-DT and MIF share specific functionalities and promote both the expression and secretion of angiogenic growth factors, e.g. CXCL8 and VEGF, from lung adenocarcinoma cells (Coleman, A. M. (2008) *J. of Immunology* 118(4):2330-2337).

Accordingly, therapies that interfere with MIF and D-DT mediated signaling are needed.

SUMMARY OF THE INVENTION

The applicant for the first time discloses antigen-binding moieties which specifically bind to MIF and D-DT. Such compounds interfering with both, MIF and D-DT are superior in terms of efficacy and provide a promising therapeutic approach. In comparison to a combination therapy using a MIF-specific and a second D-DT specific compound in parallel, bispecific or cross-reactive antigen-binding moieties which specifically bind MIF and D-DT possess several advantages. The administration of a sole therapeutic agent interacting with both, MIF and D-DT, allows much easier investigation and control of pharmacologic properties, like pharmacokinetics and pharmacodynamics, as compared to the administration of two compounds together. In addition, escape mechanisms via MIF or D-DT mediated signaling that lead to reduced efficacy can be significantly diminished by targeting both molecules in parallel. Consequently, antigen binding moieties targeting MIF and D-DT provide superior compounds for clinical development accompanied with a high medical need.

Surprisingly and despite the low sequence homology between both, MIF and D-DT, cross-reactive antibodies were successfully identified and characterized. In addition, the disclosure provides antigen binding moieties that are bispecific or cross-reactive with MIF and D-DT and neutralize or enhance the MIF and D-DT mediated signaling pathways.

The antibodies were identified upon selection strategies using recombinant MIF and recombinant D-DT protein. Based on ELISA screening binding of specific antibodies to both, MIF and D-DT, was detected. Identified clones were converted into IgG format and expressed in eukaryotic cells. After purification further characterization of the selected antibodies, $EC_{50}$ determination for MIF and D-DT, confirmed cross-reactivity to both. Additionally, further functional analyses were performed to demonstrate functional activity of the selected antibodies. MIF/D-DT cross-reactive antibodies were analyzed for the ability to inhibit binding of MIF to its receptor CD74. Furthermore, antibody-mediated inhibition of MIF-dependent release of pro-inflammatory cytokines like e.g. IL-1β and IL-6 was investigated. Consequently, an activity and efficacy of MIF/D-DT cross-reactive antibodies is predicted in human.

Although a combinatorial approach targeting MIF and D-DT was suggested (Coleman, A. M. (2008) *J. of Immunology* 118(4): 2330-2337) the identification of a sole compound which cross-reacts with both proteins was not expected as D-DT and MIF share only 33% identity and 47% homology. Large amounts of clones were screened until a MIF/D-DT cross-reactive antibody could be identified. Taken together, out 27000 clones analyzed, more than 3000 clones showed specificity for either one or both antigens, while only 3 clones proved to be MIF/D-DT cross-reactive in primary and also secondary screening steps. Using the methods disclosed, the person skilled in the art will appreciate how to identify MIF/D-DT cross-reactive antigen binding moieties and antigen binding moieties that are bispecific for MIF and D-DT.

DESCRIPTION OF THE FIGURES

FIG. 1: Comparison of amino acid sequences of MIF and D-DT from human origin. Human D-DT and human MIF share 33% of identity and 47% of homology.

DETAILED DESCRIPTION OF THE DISCLOSURE

Figure 2:
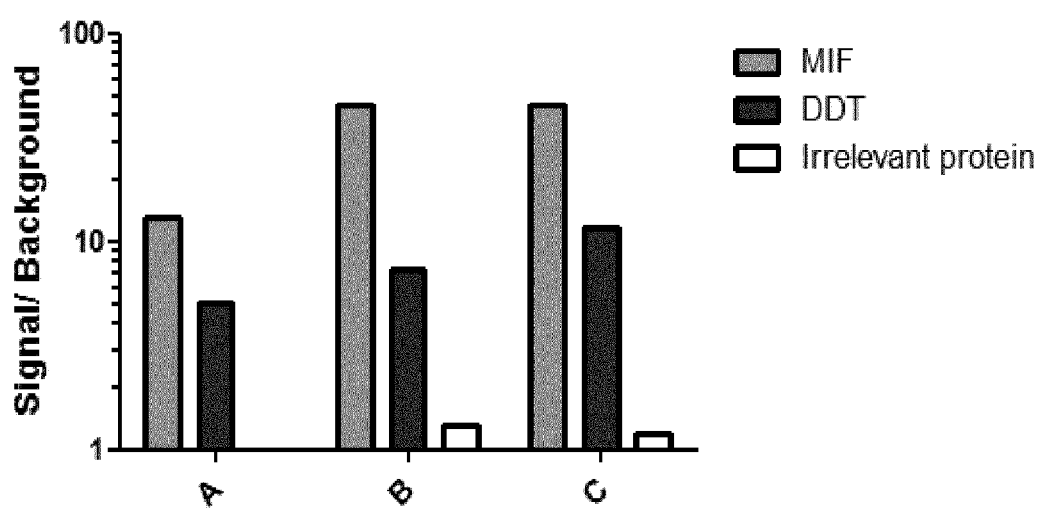
FIG. 2: Specific binding of selected MIF/D-DT cross reactive antibodies to recombinant MIF and recombinant D-DT in ELISA. Antibodies used in a concentration of 6.25 nM were applied. For all antibodies tested, more than 5-fold fluorescence intensity above background on MIF and D-DT is demonstrated. (A=MOR014093; B=MOR014116; C=MOR014138)

Accordingly, in one aspect, the disclosure pertains to an antigen-binding moiety, wherein the antigen-binding moiety specifically binds MIF and D-DT. In a preferred aspect the antigen-binding moiety specifically binds human MIF and human D-DT.

In one aspect the disclosure pertains to an antigen-binding moiety that specifically binds MIF and D-DT and wherein the antigen-binding moiety is bispecific.

In one aspect, the disclosure pertains to an isolated antigen-binding moiety, wherein the antigen-binding moiety cross-reactively binds MIF and D-DT.

In a preferred aspect the isolated antigen-binding moiety cross-reactively binds human MIF and human D-DT.

In another aspect, the disclosure pertains to an isolated antigen-binding moiety wherein the antigen-binding moiety cross-reactively binds MIF and D-DT and wherein the antigen-binding moiety is capable of specifically interfering with MIF-mediated and D-DT-mediated signal transduction. In one embodiment the isolated antigen-binding moiety is capable of specifically antagonizing MIF and D-DT-activity.

In another aspect, the disclosure pertains to an isolated antigen-binding moiety wherein the antigen-binding moiety cross-reactively binds MIF and D-DT and wherein the isolated antigen-binding moiety binds to MIF and to D-DT with an $EC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM or 1 nM.

In another aspect, the disclosure pertains to an isolated antigen-binding moiety wherein the antigen-binding moiety cross-reactively binds MIF and D-DT and wherein the isolated antigen-binding moiety binds to MIF and to D-DT with a dissociation constant ($K_D$) of less than $1\times10^7$ M$^{-1}$, $10^8$ M$^{-1}$, $10^9$ M$^{-1}$, $10^{10}$ M$^{-1}$, $10^{11}$ M$^{-1}$, $10^{12}$ M$^{-1}$ or $10^{13}$ M$^{-1}$.

In another aspect, the disclosure pertains to an isolated bispecific antigen-binding moiety wherein the bispecific antigen-binding moiety specifically binds MIF and D-DT and wherein the bispecific antigen-binding moiety is capable of specifically interfering with MIF-mediated and D-DT-mediated signal transduction. In one embodiment the isolated bispecific antigen-binding moiety is capable of specifically antagonizing MIF and D-DT-activity.

In another aspect, the disclosure pertains to an isolated bispecific antigen-binding moiety wherein the bispecific antigen-binding moiety specifically binds MIF and D-DT and wherein the isolated bispecific antigen-binding moiety binds to MIF and to D-DT with an $EC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM or 1 nM.

In another aspect, the disclosure pertains to an isolated bispecific antigen-binding moiety wherein the bispecific antigen-binding moiety cross-reactively binds MIF and D-DT and wherein the isolated bispecific antigen-binding moiety binds to MIF and to D-DT with a dissociation constant ($K_D$) of less than $1\times10^7$ M$^{-1}$, $10^8$ M$^{-1}$, $10^9$ M$^{-1}$, $10^{10}$ M$^{-1}$, $10^{11}$ M$^{-1}$, $10^{12}$ M$^{-1}$ or $10^{13}$ M$^{-1}$.

In one aspect the isolated antigen-binding moiety recognizes a conformational epitope of MIF, wherein a similar conformational epitope is present in D-DT and wherein said isolated antigen-binding moiety recognizes both conformational epitopes.

In one aspect, the disclosure pertains to an antigen-binding moiety wherein the antigen-binding moiety is an antibody or an antibody fragment. In one embodiment said antibody or fragment thereof is a monoclonal antibody or a polyclonal antibody. In one embodiment said antibody or an antibody fragment is a human or humanized antibody. In one embodiment said antibody or an antibody fragment is a chimeric antibody. In one embodiment said antibody or an antibody fragment comprises a human heavy chain constant region and a human light chain constant region. In one embodiment said antibody or an antibody fragment is an IgG isotype. In another embodiment the antibodies can be of any isotype (e.g., IgG, IgE, IgM, IgD, and IgA), class (e.g., IgG1, IgG2, IgG3, IgG4, IgA1 and IgA2) or derivative thereof (e.g. IgG1f LALA). In one embodiment the antibodies are of IgG1f LALA isotype. In one embodiment said antibody or an antibody fragment is selected from the group consisting of a Fab, F(ab2)', F(ab)2' and scFV. In one embodiment the antibody is selected from the group consisting of a monoclonal antibody, a polyclonal antibody, a chimeric antibody, a humanized antibody, and a synthetic antibody. In one embodiment, the antibody or fragment thereof is a human or humanized antibody.

In one embodiment, the disclosure pertains to an antibody or fragment thereof wherein said antibody or fragment thereof cross-reactively binds MIF and D-DT and comprises two identical antigen binding regions. In one embodiment, the antibody or fragment thereof comprises two antigen binding regions wherein each of said antigen binding regions cross-reactively binds MIF and D-DT. In one embodiment, the antibody or fragment thereof comprises two heavy (H) chains and two light (L) chains wherein each heavy chain and each light chain are identical.

In one embodiment, the antibody or fragment thereof cross-reactively binds MIF and D-DT and comprises two antigen binding regions wherein each of said antigen binding regions comprises six CDRs and wherein the HCDR3 of both antigen binding regions is identical. In one embodiment, the antibody or fragment thereof cross-reactively binds MIF and D-DT and comprises two antigen binding regions wherein each of said antigen binding region comprises six CDRs. In one embodiment, the antibody or fragment thereof cross-reactively binds MIF and D-DT and comprises two antigen binding regions wherein each of said antigen binding regions comprises the same set of six CDRs.

In one embodiment, the antibody or fragment thereof cross-reactively binds MIF and D-DT and comprises two antigen binding regions wherein each of said antigen binding regions comprises the same variable regions of the heavy chain (abbreviated herein as VH) and the light chain (abbreviated herein as VL). In one embodiment, the antibody or fragment thereof cross-reactively binds MIF and D-DT and comprises two antigen binding regions wherein the two antigen binding regions share the same HCDR1, the same HCDR2, the same HCDR3, the same LCDR1, the same LCDR2 and the same LCDR3.

In one embodiment said antibody or an antibody fragment is selected from the group consisting of a Fab, F(ab2)', F(ab)2' and scFV.

In one aspect, the disclosure pertains to an antigen-binding moiety wherein the antigen-binding moiety is an antibody-derived scaffold. In one embodiment the antibody-derived scaffold is a bispecific antibody-derived scaffold. In one embodiment the bispecific antibody-derived scaffold is selected from the group consisting of a bispecific-scFv, a tetravalent bispecific antibody, a cross-linked Fab or a bispecific IgG.

In one embodiment, the antibody or fragment thereof is a single chain antibody. In one embodiment, the antibody or fragment thereof is bispecific. In one embodiment the antibody or fragment thereof is a bispecific antibody-derived scaffold wherein said bispecific antibody-derived scaffold is selected from the group consisting of a bispecific-scFv, a tetravalent bispecific antibody, a cross-linked Fab or a bispecific IgG.

In one aspect, the disclosure pertains to an isolated antigen-binding moiety, wherein the antigen-binding moiety cross-reactively binds MIF and D-DT and wherein said antigen-binding moiety is selected from the group consisting of single domain antibodies, maxibodies, minibodies, intrabodies, diabodies, triabodies, tetrabodies, v-NAR, camelid antibodies, ankyrins, domain antibodies, lipocalins, small modular immuno-pharmaceuticals, maxybodies, Protein A and affilins.

In one embodiment of the disclosure the cross-reactive antigen binding moiety under physiological conditions either binds MIF or D-DT. In one embodiment of the disclosure the cross-reactive antigen binding moiety under physiological conditions simultaneously binds to MIF and D-DT. In one embodiment of the disclosure the cross-reactive antigen binding moiety under physiological conditions either binds MIF or D-DT or simultaneously binds to MIF and D-DT.

In one aspect, the disclosure pertains to an isolated antigen-binding moiety, wherein the antigen-binding moiety cross-reactively binds MIF and D-DT and wherein said antigen-binding moiety binds to human MIF and human D-DT and additionally to cynomolgus MIF and cynomolgus D-DT. In one aspect, the disclosure pertains to an isolated antigen-binding moiety, wherein the antigen-binding moiety cross-reactively binds MIF and D-DT and wherein said antigen-binding moiety binds to human MIF and human D-DT and additionally to cynomolgus MIF or cynomolgus D-DT.

In one aspect, the disclosure pertains to an isolated antigen-binding moiety, wherein the antigen-binding moiety cross-reactively binds MIF and D-DT and wherein said antigen-binding moiety binds to human MIF and human D-DT and to murine MIF and murine D-DT. In one aspect, the disclosure pertains to an isolated antigen-binding moiety, wherein the antigen-binding moiety cross-reactively binds MIF and D-DT and wherein said antigen-binding moiety binds to human MIF and human D-DT and to murine MIF or murine D-DT.

In one aspect, the disclosure pertains to an isolated antigen-binding moiety, wherein the antigen-binding moiety cross-reactively binds MIF and D-DT and wherein said antigen-binding moiety binds to human MIF and human D-DT and to rat MIF and rat D-DT. In one aspect, the disclosure pertains to an isolated antigen-binding moiety, wherein the antigen-binding moiety cross-reactively binds MIF and D-DT and wherein said antigen-binding moiety binds to human MIF and human D-DT and to rat MIF or rat D-DT.

In one embodiment, the antibody or fragment thereof cross-reactively binds to mammalian MIF and mammalian D-DT. In one embodiment mammalian MIF and mammalian D-DT are from species which are selected from a list which consist of human, murine, rat, rhesus monkey (*Macaca mulatta*) and cynomolgus (*Macaca fascicularis*).

In one embodiment, the antibody or fragment thereof cross-reactively binds to human MIF and human D-DT. In one embodiment, the antibody or fragment thereof cross-reactively binds to mouse MIF and mouse D-DT. In one embodiment, the antibody or fragment thereof cross-reactively binds to rat MIF and rat D-DT. In one embodiment, the antibody or fragment thereof cross-reactively binds to rhesus monkey (*Macaca mulatta*) MIF and rhesus monkey (*Macaca mulatta*) D-DT. In one embodiment, the antibody or fragment thereof cross-reactively binds to cynomolgus MIF and cynomolgus D-DT.

In one aspect, the disclosure pertains to an isolated antibody or fragment thereof that cross-reactively binds MIF and D-DT comprising 6 CDRs defined by Kabat or Chothia of any of the antibodies in Table 1.

In another aspect, the disclosure pertains to an antibody or fragment thereof that cross-reactively binds MIF and D-DT, and cross-competes with an antibody described in Table 1.

In a certain embodiment, the antibody that cross-competes with an antibody described in Table 1 reduces the binding of one of the antibodies described in Table 1 to MIF or D-DT by at least 20%, 30%, 40%, 50%, 60%, 70%, 80% or 90% in an ELISA-based cross-competition.

In a certain embodiment, the antibody that cross-competes with an antibody described in Table 1 reduces the binding of one of the antibodies described in Table 1 to MIF or D-DT by at least 20%, 30%, 40%, 50%, 60%, 70%, 80% or 90% in an ELISA-based cross-competition assay according to Example 6 in comparison to the positive control.

In another aspect, the disclosure pertains to an antibody or fragment thereof that cross-reactively binds MIF and D-DT and interacts with (e.g., by binding, stabilizing, spatial distribution) the same epitope as an antibody described in Table 1.

In a certain embodiment, the antibody that binds to the same epitope on MIF and D-DT as the antibodies of the present disclosure is a human monoclonal antibody. In a certain embodiment, the antibody that binds to the same linear epitope on MIF and D-DT as the antibodies of the present disclosure is a human monoclonal antibody. In a certain embodiment, the antibody that binds to the same conformational epitope on MIF and D-DT as the antibodies of the present disclosure is a human monoclonal antibody. Such human monoclonal antibodies can be prepared and isolated as described herein.

In another aspect, the disclosure pertains to an isolated antibody or fragment thereof comprising a heavy chain CDR3 selected from the group consisting of SEQ ID NO: 3, SEQ ID NO: 9, SEQ ID NO: 19, SEQ ID NO: 25, SEQ ID NO: 35 and SEQ ID NO: 41.

In another aspect, the disclosure pertains to an isolated antibody or fragment thereof comprising a VH comprising SEQ ID NO: 14 and a VL comprising SEQ ID NO: 13.

In another aspect, the disclosure pertains to an isolated antibody or fragment thereof comprising a VH comprising SEQ ID NO: 30 and a VL comprising SEQ ID NO: 29.

In another aspect, the disclosure pertains to an isolated antibody or fragment thereof comprising a VH comprising SEQ ID NO: 46 and a VL comprising SEQ ID NO: 45.

In another aspect, the disclosure pertains to an isolated antibody or fragment thereof, comprising heavy chain variable region CDR1 of SEQ ID NO: 1; CDR2 of SEQ ID NO: 2; CDR3 of SEQ ID NO: 3; a light chain variable region CDR1 of SEQ ID NO: 4; CDR2 of SEQ ID NO: 5; and CDR3 of SEQ ID NO: 6.

In another aspect, the disclosure pertains to an isolated antibody or fragment thereof, comprising a heavy chain variable region CDR1 of SEQ ID NO: 17; CDR2 of SEQ ID NO: 18; CDR3 of SEQ ID NO: 19; a light chain variable region CDR1 of SEQ ID NO: 20; CDR2 of SEQ ID NO: 21; and CDR3 of SEQ ID NO: 22.

In another aspect, the disclosure pertains to an isolated antibody or fragment thereof, comprising a heavy chain variable region CDR1 of SEQ ID NO: 33; CDR2 of SEQ ID NO: 34; CDR3 of SEQ ID NO: 35; a light chain variable region CDR1 of SEQ ID NO: 36; CDR2 of SEQ ID NO: 37; and CDR3 of SEQ ID NO: 38.

In another aspect, the disclosure pertains to a pharmaceutical composition comprising an antibody or fragment of the present disclosure and a pharmaceutically acceptable carrier.

In another aspect, the disclosure pertains to an isolated antigen-binding moiety, wherein the antigen-binding moiety cross-reactively binds MIF and D-DT and wherein said isolated antigen-binding moieties are used as a drug.

In another aspect, the disclosure pertains to an antibody or fragment thereof that cross-reactively binds MIF and D-DT, and cross-competes with an isolated antibody or fragment thereof, comprising heavy chain variable region CDR1 of SEQ ID NO: 1; CDR2 of SEQ ID NO: 2; CDR3 of SEQ ID NO: 3; a light chain variable region CDR1 of SEQ ID NO: 4; CDR2 of SEQ ID NO: 5; and CDR3 of SEQ ID NO: 6.

In another aspect, the disclosure pertains to an antibody or fragment thereof that cross-reactively binds MIF and D-DT, and cross-competes with an isolated antibody or fragment thereof, comprising a heavy chain variable region CDR1 of SEQ ID NO: 17; CDR2 of SEQ ID NO: 18; CDR3 of SEQ ID NO: 19; a light chain variable region CDR1 of SEQ ID NO: 20; CDR2 of SEQ ID NO: 21; and CDR3 of SEQ ID NO: 22.

In another aspect, the disclosure pertains to an antibody or fragment thereof that cross-reactively binds MIF and D-DT, and cross-competes with an isolated antibody or fragment thereof, comprising a heavy chain variable region CDR1 of SEQ ID NO: 33; CDR2 of SEQ ID NO: 34; CDR3 of SEQ ID NO: 35; a light chain variable region CDR1 of SEQ ID NO: 36; CDR2 of SEQ ID NO: 37; and CDR3 of SEQ ID NO: 38.

In another aspect, the disclosure pertains to an antibody or fragment thereof that cross-reactively binds MIF and D-DT, and reduces the binding of an isolated antibody or fragment thereof, comprising heavy chain variable region CDR1 of SEQ ID NO: 1; CDR2 of SEQ ID NO: 2; CDR3 of SEQ ID NO: 3; a light chain variable region CDR1 of SEQ ID NO: 4; CDR2 of SEQ ID NO: 5; and CDR3 of SEQ ID NO: 6 by at least 20%, 30%, 40%, 50%, 60%, 70%, 80% or 90% in comparison to the positive control in an ELISA-based cross-competition assay according to Example 6.

In another aspect, the disclosure pertains to an antibody or fragment thereof that cross-reactively binds MIF and D-DT, and reduces the binding of an isolated antibody or fragment thereof, comprising heavy chain variable region CDR1 of SEQ ID NO: 17; CDR2 of SEQ ID NO: 18; CDR3 of SEQ ID NO: 19; a light chain variable region CDR1 of SEQ ID NO: 20; CDR2 of SEQ ID NO: 21; and CDR3 of SEQ ID NO: 22 by at least 20%, 30%, 40%, 50%, 60%, 70%, 80% or 90% in comparison to the positive control in an ELISA-based cross-competition assay according to Example 6.

In another aspect, the disclosure pertains to an antibody or fragment thereof that cross-reactively binds MIF and D-DT, and reduces the binding of an isolated antibody or fragment thereof, comprising heavy chain variable region CDR1 of SEQ ID NO: 33; CDR2 of SEQ ID NO: 34; CDR3 of SEQ ID NO: 35; a light chain variable region CDR1 of SEQ ID NO: 36; CDR2 of SEQ ID NO: 37; and CDR3 of SEQ ID NO: 38 by at least 20%, 30%, 40%, 50%, 60%, 70%, 80% or 90% in comparison to the positive control in an ELISA-based cross-competition assay according to Example 6.

In another aspect, the disclosure pertains to an antibody or fragment thereof that cross-reactively binds MIF and D-DT and interacts with (e.g., by binding, steric hinderance, stabilizing/destabilizing, spatial distribution) the same epitope as an isolated antibody or fragment thereof, comprising heavy chain variable region CDR1 of SEQ ID NO: 1; CDR2 of SEQ ID NO: 2; CDR3 of SEQ ID NO: 3; a light chain variable region CDR1 of SEQ ID NO: 4; CDR2 of SEQ ID NO: 5; and CDR3 of SEQ ID NO: 6.

In another aspect, the disclosure pertains to an antibody or fragment thereof that cross-reactively binds MIF and D-DT and interacts with (e.g., by binding, steric hinderance, stabilizing/destabilizing, spatial distribution) the same epitope as an isolated antibody or fragment thereof, comprising a heavy chain variable region CDR1 of SEQ ID NO: 17; CDR2 of SEQ ID NO: 18; CDR3 of SEQ ID NO: 19; a light chain variable region CDR1 of SEQ ID NO: 20; CDR2 of SEQ ID NO: 21; and CDR3 of SEQ ID NO: 22.

In another aspect, the disclosure pertains to an antibody or fragment thereof that cross-reactively binds MIF and D-DT and interacts with (e.g., by binding, steric hinderance, stabilizing/destabilizing, spatial distribution) the same epitope as an isolated antibody or fragment thereof, comprising a heavy chain variable region CDR1 of SEQ ID NO: 33; CDR2 of SEQ ID NO: 34; CDR3 of SEQ ID NO: 35; a light chain variable region CDR1 of SEQ ID NO: 36; CDR2 of SEQ ID NO: 37; and CDR3 of SEQ ID NO: 38.

In another aspect, the disclosure pertains to a nucleic acid wherein the nucleic acid comprises a VH comprising SEQ ID NO: 16 and a VL comprising SEQ ID NO: 15.

In another aspect, the disclosure pertains to a nucleic acid wherein the nucleic acid comprises a VH comprising SEQ ID NO: 32 and a VL comprising SEQ ID NO: 31.

In another aspect, the disclosure pertains to a nucleic acid wherein the nucleic acid comprises a VH comprising SEQ ID NO: 48 and a VL comprising SEQ ID NO: 47.

In another aspect, the disclosure pertains to a nucleic acid sequence encoding an isolated antigen-binding moiety that cross-reactively binds MIF and D-DT having at least 75%, 80%, 85%, 90%, 95%, 98%, 99% sequence identity to nucleic acids selected from the group consisting of SEQ ID NO: 15, SEQ ID NO: 16, SEQ ID NO: 31, SEQ ID NO: 32, SEQ ID NO: 47 and SEQ ID NO: 48.

In another aspect, the disclosure pertains to a vector comprising a nucleic acid selected from the group consisting of SEQ ID NO: 15, SEQ ID NO: 16, SEQ ID NO: 31, SEQ ID NO: 32, SEQ ID NO: 47 and SEQ ID NO: 48.

In another aspect, the disclosure pertains to an isolated host cell comprising a vector wherein said vector comprises a nucleic acid selected from the group consisting of SEQ ID NO: 15, SEQ ID NO: 16, SEQ ID NO: 31, SEQ ID NO: 32, SEQ ID NO: 47 and SEQ ID NO: 48 and wherein said host cell is able to express the polypeptide encoded by the vector.

In another aspect, the disclosure pertains to an isolated host cell comprising a vector wherein said vector comprises a nucleic acid selected from the group consisting of SEQ ID NO: 15, SEQ ID NO: 16, SEQ ID NO: 31, SEQ ID NO: 32, SEQ ID NO: 47 and SEQ ID NO: 48 and wherein said host cell is able to express the polypeptide encoded by the vector and wherein said host cell is a mammalian cell.

In another aspect, the disclosure pertains to an isolated host cell comprising a vector wherein said vector comprises a nucleic acid selected from the group consisting of SEQ ID NO: 15, SEQ ID NO: 16, SEQ ID NO: 31, SEQ ID NO: 32, SEQ ID NO: 47 and SEQ ID NO: 48 and wherein said host cell is able to express the polypeptide encoded by the vector and wherein said host cell is a human cell.

In another aspect, the disclosure pertains to a kit comprising an isolated antigen-binding moiety that cross-reactively binds MIF and D-DT.

Definitions

In order that the present disclosure may be more readily understood, certain terms are first defined. Additional definitions are set forth throughout the detailed description.

The term "MIF" refers to MIF as defined in Accession No.: CAG30406.1 and is encoded by the amino acid sequence:

The phrase "signal transduction" or "signaling activity" as used herein refers to a biochemical causal relationship generally initiated by a protein-protein interaction such as binding of a growth factor to a receptor, resulting in transmission of a signal from one portion of a cell to another portion of a cell. Interaction of a ligand with a respective receptor leads to phosphorylation of one or more tyrosine, serine, or threonine residues on one or more proteins in the series of reactions causing signal transduction. Signaling transduction processes typically include nuclear events, resulting in a change in gene expression. For example, for extracellular MIF, the transmission involves specific interaction of extracellular MIF with receptors presented on the surface of specific cell populations. Receptors for extracellular MIF are e.g., but not limited to that, CD74, CD74/CD44 and chemokine receptors like CXCR2 and CXCR4. Thereby signal transduction upon interaction of MIF with a respective receptor promotes the production of angiogenic factors like VEGF and CXCL8. Accordingly, receptors for extracellular D-DT upon their interaction with D-DT induce signal transduction which results e.g. but not limited to that in the production of angiogenic factors like VEGF and CXCL8.

The phrase "antagonist" as used herein refers to an antigen binding moiety that neutralizes the biological activity of an antigen. The phrase "antagonize" is used in this context accordingly. For example, an antagonist interferes with the signal transduction which is mediated by an antigen. Examples of assays to determine antagonistic activity are described in more details in the examples below. In some embodiments, the antibodies of the present disclosure reduce, decrease or inhibit interaction of MIF to CD74. In some embodiments, the antibodies reduce, decrease or inhibit MIF-dependent release of pro-inflammatory cytokines (e.g. IL-1β, IL-6). In some embodiments, the activities of the antibodies can be measured by binding to MIF and D-DT using for example SET, ELISA, FACS or BIAcore.

The term "valency" as used herein refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different molecules, e.g., different antigens, or different epitopes on the same molecule). The terms "monovalent" and "bivalent" are used in this context accordingly.

The term "antigen binding moiety", as used herein, refers to a moiety which comprises a polypeptide that confers the ability to specifically bind to a given antigen (e.g. MIF and D-DT). For example, antibodies, antibody derivatives, antibody-like scaffolds and alternative scaffolds comprise at least one antigen binding moiety. Antigen binding moieties can also be incorporated into single domain antibodies, maxibodies, minibodies, intrabodies, diabodies, triabodies, tetrabod-

```
SEQ-ID: 49:
1   MPMFIVNTNV  PRASVPDGFL  SELTQQLAQA  TGKPPQYIAV  HVVPDQLMAF  GGSSEPCALC
61  SLHSIGKIGG  AQNRSYSKLL  CGLLAERLRI  SPDRVYINYY  DMNAANVGWN  NSTFA
```

The term "D-DT" refers to D-DT as defined in Accession No. NP_001346 and is encoded by the amino acid sequence:

ies, v-NAR and bispecific-scFv (see, e.g., Hollinger and Hudson, 2005, Nature Biotechnology, 23, 9, 1126-1136). Further

```
SEQ-ID NO: 50:
1   MPFLELDTNL  PANRVPAGLE  KRLCAAAASI  LGKPADRVNV  TVRGLAMAL   SGSTEPCAQL
61  SISSIGVVGT  AEDNRSHSAH  FFEFLTKELA  LGQDRILIRF  FPLESWQIGK  IGTVMTFL
``` examples of molecules comprising antigen binding moieties are given herein below and include fibronectin (Adnexus, fully owned by Bristol-Myers Squibb, Waltham, Mass.), camelid antibodies, ankyrins (Molecular Partners AG, Zurich, Switzerland), domain antibodies (Domantis, Ltd., Cambridge, Mass., and Ablynx nv, Zwijnaarde, Belgium), lipocalins (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilins (gamma-crystallin or ubiquitin) (Scil Proteins GmbH, Halle, Germany).

The term "antibody" as used herein includes whole antibodies and any fragment or single chains thereof. A naturally occurring "antibody" is a protein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., IgG1, IgG2, IgG3, IgG4, IgA1 and IgA2), subclass or modified version thereof (e.g. IgG1f LALA).

The terms "heavy chain variable region CDR1" and "H-CDR1" are used interchangeably, as are the terms "heavy chain variable region CDR2" and "H-CDR2", the terms "heavy chain variable region CDR3" and "H-CDR3", the terms "light chain variable region CDR1" and "L-CDR1"; the terms "light chain variable region CDR2" and "L-CDR2" and the terms "light chain variable region CDR3" and "L-CDR3"

Antigen binding can be performed by "fragments" of an intact antibody. Examples of binding fragments encompassed within the term "antibody fragment" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., (1989) *Nature* 341:544-546), which consists of a VH domain; and an isolated complementary determining region (CDR).

A "single chain Fragment (scFv)" is a single protein chain in which the VL and VH regions pair to form monovalent molecules (known as single chain Fv (scFv); see, e.g., Bird et al., (1988) *Science* 242:423-426; and Huston et al., (1988) *Proc. Natl. Acad. Sci.* 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies.

The term "epitope" includes any proteinacious region which is specifically recognized by an immunoglobulin or T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope. An epitope can comprise those residues to which the antibody binds and may be "linear" or "conformational."

The term "linear epitope" refers to an epitope with all of the points of interaction between the protein and the interacting molecule (such as an antibody) occur linearly along the primary amino acid sequence of the protein (continuous).

The term "conformational epitope" refers to an epitope in which discontinuous amino acids along the primary amino acid sequence of the protein come together in three dimensional conformations. In a conformational epitope, the points of interaction occur across amino acid residues on the protein that are separated from one another.

The term "cross-competes" refers to antigen binding moieties (such as antibodies) which share the ability to bind to a specific region of an antigen. In the present disclosure an antigen binding moiety that is "cross-competitive" has the ability to interfere with the binding of another antigen binding moiety for MIF and/or D-DT in a standard competitive binding assay. Such an antibody may, according to non-limiting theory, bind to the same or a related or nearby (e.g., a structurally similar or spatially proximal) epitope on the MIF and D-DT protein as the antibody with which it competes. Cross-competition studies to find antibodies that competitively bind with one another, e.g., the antibodies compete for binding to the antigen can be performed. For example the present disclosure provides antibodies that cross-compete with (e.g., by binding, stabilizing, spatial distribution) the antibodies described in Table 1. Such an antibody may, according to non-limiting theory, bind to the same or a related or nearby (e.g., a structurally similar or spatially proximal) epitope on the MIF or D-DT protein as the antibody with which it competes. The ability or extent to which an antibody or other binding agent is able to interfere with the binding of another antibody or binding molecule to MIF or D-DT and therefore whether it can be said to cross-compete according to the invention, can be determined using standard competition binding assays. Cross-competition is present if antibody A reduces binding of antibody B at least by 60%, specifically at least by 70% and more specifically at least by 80% and vice versa in comparison to the positive control which lacks one of said antibodies. As the skilled artisan appreciates competition may be assessed in different assay set-ups. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competition uses an ELISA-based approach (e.g. Example 6). Furthermore a high throughput process for "binning" antibodies based upon their cross-competition is described in International Patent Application No. WO2003/48731. Cross-competition is present if the antibody under investigation reduces the binding of one of the antibodies described in Table 1 by 60% or more, specifically by 70% or more and more specifically by 80% or more and if one of the antibodies described in Table 1 reduces the binding of said antibody to MIF or D-DT by 60% or more, specifically by 70% or more and more specifically by 80% or more.

The term "human antibody", as used herein, is intended to include antibodies having variable regions in which both the framework and CDR regions are derived from sequences of human origin. As used herein, a human antibody comprises heavy or light chain variable regions or full length heavy or light chains. In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Thereby said human antibody can be obtained from technology platforms which comprise antibodies derived from human germline genes either generated by PCR-amplification of VH/VL repertoire isolated from B-cells or are generated synthetically. Technology platforms include library based approaches comprising human immunoglobulin genes displayed on phage, ribosome or yeast. Respective display technologies are standard in the scientific community. Furthermore immunization of a transgenic mouse carrying human immunoglobulin repertoire is another approach to generate human antibodies against an antigen of interest. Antibodies or fragments thereof selected from an antibody library based on the MorphoSys HuCAL® concept (Knappik et al., (2000) J Mol Biol 296:57-86) are considered as fully human.

The terms "monoclonal antibody" as used herein refer to a preparation of antibody molecules of single molecular composition. A monoclonal antibody composition displays a unique binding site having a unique binding specificity and affinity for particular epitopes.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al (1994) *Proc. Natl. Acad. Sci. USA*, 81:6851-6855; Morrison and Oi (1988) *Adv. Immunol.*, 44:65-92; Verhoeyen et al. (1988) *Science*, 239:1534-1536; Padlan, Molec (1991) *Immun.*, 28:489-498; and Padlan, Molec (1994) *Immun.*, 31:169-217. Other examples of human engineering technology include, but are not limited to Xoma technology disclosed in U.S. Pat. No. 5,766,886.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "isolated" refers to a compound which can be e.g. an antibody or an antigen binding moiety that is substantially free of other antibodies or antigen binding moieties having different antigenic specificities. Moreover, an isolated antibody antigen binding moiety may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors. For example IgG1f LALA is a modified version of the IgG isotype having significantly reduced effector functions. Specific substitutions of amino acids reduced the binding affinity for Fc gamma RI receptor as compared with unmodified antibody. IgG1f LALA is described in U.S. Ser. No. 08/479,752 (SCOTGEN BIOPHARMACEUTICALS INC.) which is incorporated by reference in its entirety. In certain embodiments of the present disclosure the antigen-binding moieties of are antibodies and are of the type IgG, IgM, IgA, IGE or IgD. In specific embodiments the antibodies are of the type IgG. In certain embodiments of the present disclosure the antibodies are of the subtype IgG1, IgG2, IgG3 or IgG4. In specific embodiments the antibodies are of the subtype IgG1 or IgG4. In other specific embodiments the antibodies are of the subtype IgG1 or IgG1f LALA.

The phrase "specifically binds" or "selectively binds" to an antigen (e.g., a MIF-binding antibody) refers to a binding reaction that is determinable in the presence of an antigen (e.g., human MIF or human D-DT) in a heterogeneous population of proteins and other biologics. Thereby the phrases "recognizing an antigen" and "specific for an antigen" are used interchangeably herein with the term "binds specifically to an antigen". Specific binding of an antigen binding moiety, like e.g. a monoclonal antibody, to an antigen can be determined by various established methods known in the art and include ELISA, FACS, Western Blot, Immuno Blot, BIAcore and SET. In the present disclosure an antigen binding moiety is deemed to be specific for an antigen or a selection of more than one antigen if the antigen binding moiety is demonstrated to be able to bind to a specific antigen or a selection of more than one antigen at least 2-fold, at least 3-fold, at least 4-fold, at least 5-fold, at least 6-fold, at least 7-fold, at least 8-fold, at least 9-fold, at least 10-fold, at least 20-fold, over background. Thereby the background is determined by an antigen binding moiety which is known to be unspecific for the selected antigens or by comparison to binding to an unrelated antigen.

In the present disclosure an antigen binding moiety is deemed to be specific for an antigen if the $EC_{50}$ of the antigen binding moiety is determined to be less than 100 nM, less than 90 nM, less than 80 nM, less than 70 nM, less than 60 nM, less than 50 nM, less than 40 nM, less than 30 nM, less than 29 nM, less than 28 nMm, less than 27 nM, less than 26 nM, less than 25 nM, less than 24 nM, less than 23 nM, less than 22 nM, less than 21 nM, less than 20 nM, less than 15 nM less than 10 nM, less than 5 nM less than 4 nM, less than 3 nM, less than 2 nM, less than 1 nM for each of the respective antigens. $EC_{50}$ can be determined according to the specification stated hereafter.

The term "affinity" as used herein refers to the strength of interaction between an antigen binding moiety, like e.g. a monoclonal antibody and an antigen at single antigenic sites. Within each antigenic site, the variable region of the antibody "arm" interacts through weak non-covalent forces with antigen at numerous sites; the more interactions, the stronger the affinity.

The term "$K_D$", as used herein, refers to the dissociation constant, which is obtained from the ratio of $K_d$ to $K_a$ (i.e. $K_d/K_a$) and is expressed as a molar concentration (M). $K_D$ values for antigen binding moieties like e.g. monoclonal antibodies can be determined using methods well established in the art. Methods for determining the $K_D$ of an antigen binding moiety like e.g. a monoclonal antibody are SET (soluble equilibrium titration) or surface plasmon resonance using a biosensor system such as a Biacore® system. In the present disclosure a MIF/D-DT cross-reactive antibody typically has a dissociation rate constant ($K_D$) ($k_{off}/k_{on}$) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$M, less than $10^{-10}$ M less than $5\times10^{-11}$M, less than $10^{-11}$M, less than $5\times10^{-12}$ M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower.

The term "antigen binding region" as used herein refers to a domain of an antigen binding moiety that is responsible for the specific binding between an antigen binding moiety and an antigen. For example, the antigen binding region of an antibody or a fragment thereof is formed by amino acid residues of the N-terminal variable regions of the heavy chain (abbreviated herein as VH) and the light chain (abbreviated herein as VL). The variable regions of the VH and the VL each comprise three hypervariable regions, termed complementary determining regions (CDR). The 3 CDRs of the VH and the 3 CDRs of the VL are three-dimensionally disposed relative to each other to form an antigen binding surface.

The phrase "cross-reactively binds" and the terms "cross-specific" and "cross-reactive" are used herein interchangeably and refer to an antigen binding region which has the ability to specifically bind to more than one antigen. For example, in the present disclosure the antigen binding region cross-reactively binds to MIF and D-DT. Preferably, the antigen binding region cross-specifically binds to human MIF and human D-DT. For example, in the present disclosure an antibody that cross-reactively binds to MIF and D-DT comprises two arms wherein both arms comprise the same antigen binding region.

In the present disclosure the phrases "cross-specifically binds to MIF and D-DT" and "MIF/D-DT cross-reactive" are used herein interchangeably and refer to an antigen binding moiety which cross-reactively binds to MIF and D-DT. Antigen specificity is defined above and can be determined by methods known to one of skill in the art like e.g. ELISA, FACS, Western Blot, Immuno Blot, BIAcore or SET. In the present disclosure an antigen binding moiety is deemed to be cross-reactive to an unlimited number of antigens if the antigen binding moiety is demonstrated to be able to bind to a specific selection of at least two antigens at least 2-fold, at least 3-fold, at least 4-fold, at least 5-fold, at least 6-fold, at least 7-fold, at least 8-fold, at least 9-fold, at least 10-fold, at least 20-fold, over background. Thereby the background is determined by an antigen binding moiety which is known to be unspecific for the selected antigens or by comparison to binding to an unrelated antigen.

In the present disclosure an antigen binding moiety is deemed to be cross-reactive to an unlimited number of antigens if the $EC_{50}$ of the antigen binding moiety is determined to be less than 100 nM, less than 90 nM, less than 80 nM, less than 70 nM, less than 60 nM, less than 50 nM, less than 40 nM, less than 30 nM, less than 29 nM, less than 28 nMm, less than 27 nM, less than 26 nM, less than 25 nM, less than 24 nM, less than 23 nM, less than 22 nM, less than 21 nM, less than 20 nM, less than 15 nM less than 10 nM, less than 5 nM less than 4 nM, less than 3 nM, less than 2 nM, less than 1 nM for each of the respective antigens. $EC_{50}$ can be determined according to the specification stated hereafter.

In the present disclosure cross-reactivity of the antigen binding moieties is not limited to one species. In the present disclosure an antigen binding moiety that cross-specifically binds to human MIF and human D-DT additionally cross-reacts to MIF and/or D-DT derived from one or more other mammalian species (e.g. murine, rat, rhesus monkey and cynomolgus).

The term "bispecific" is used herein to refer to an antibody, an antibody derivative, an antibody-like scaffold or an alternative scaffold which comprises two different antigen binding regions wherein each of the incorporated antigen binding regions bears individual binding specificity to a specific antigen. For example, in the present disclosure a bispecific molecule comprises one antigen binding region which cross-reactively binds MIF and D-DT and a second antigen binding region which specifically binds to a further antigen. Antigen binding regions can be incorporated into bispecific antibody-derived scaffolds. Examples thereof are given herein below and include bispecific-scFv (BITE®; Micromet, Rockville, Md.), tetravalent bispecific antibody formats (TandAb®, Affimed Therapeutics AG, Heidelberg, Germany), cross-linked Fabs and bispecific IgGs (TRION Pharma GmbH, Munich, Germany).

The term "amino acid" refers to naturally occurring and also synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; and Rossolini et al. (1994) *Mol. Cell. Probes* 8:91-98).

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

Accordingly, an antibody that "inhibits" one or more functional properties of MIF and/or D-DT (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present).

The phrases "percent identical" or "percent identity", in the context of two or more nucleic acids or polypeptide sequences, refers to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Additionally or alternatively, the protein sequences of the present disclosure can further be used as a "query sequence" to perform a search against public databases to, for example, identifies related sequences. For example, such searches can be performed using the BLAST program (version 2.0) of Altschul et al. (1990) *J. Mol. Biol.* 215:403-10. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Two examples of algorithms that are suitable for determining percent sequence identity and sequence similarity are the BLAST and BLAST 2.0 algorithms, which are described in Altschul et al., (1977) *Nuc. Acids Res.* 25:3389-3402; and Altschul et al., (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (*Comput. Appl. Biosci.* 4:11-17 (1988)) which has been incorporated into the ALIGN program (version 2.0), using a PAM 120 weight residue table, a gap length penalty of 12 and a gap penalty of 4. In addition, the percent identity between two amino acid sequences can be determined using the Needleman and Wunsch (*J. Mol, Biol.* 48:444-453 (1970)) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Various aspects of the disclosure are described in further detail in the following sections and subsections.

Engineered and Modified Antibodies

An antibody of the present disclosure can be a modified antibody derived from the antibodies shown in Table 1. Thereby the antibodies shown in Table 1 are used as starting material to engineer a modified antibody.

An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

By engineering or modify an antibody improved variants of the parental clone can be achieved. Meanwhile various technologies e.g. to improve the affinity, to reduce immunogenicity and to increase the effector function of an antibody are established in the art.

Antibodies interact with target antigens predominantly through amino acid residues that are located in the six heavy and light chain complementarity determining regions (CDRs). Thus affinity maturation comprises the modification of specific CDRs to alter binding properties of an antibody. Affinity maturation includes site directed mutagenesis within the hypervariable regions and may comprise amino acid substitutions, additions or deletions. Another type of affinity maturation comprises the complete replacement of specific CDRs in a specific antibody with a library of respective CDRs. Modified antibodies thereupon can be analyzed in standard antigen binding assays (e.g. ELISA, FACS, BiaCore, SET analysis) for improved affinity to the respective antigen. (see, e.g., Riechmann et al., (1998) *Nature* 332:323-327; Jones et al., (1986) *Nature* 321:522-525; Queen et al., (1989) *Proc. Natl. Acad., U.S.A.* 86:10029-10033; U.S. Pat. No. 5,225,539 to Winter, and U.S. Pat. Nos. 5,530,101; 5,585, 089; 5,693,762 and 6,180,370 to Queen et al.)

Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Such framework sequences can be obtained from public DNA databases or published references that include germline antibody gene sequences. For example, germline DNA sequences for human heavy and light chain variable region genes can be found in the "Vase" human germline sequence database (available on the Internet at www.mrc-cpe.cam.ac.uk/vbase), as well as in Kabat et al., (1991) Sequences of Proteins of Immunological Interest, Fifth Edition, U.S. Department of Health and Human Services, NIH Publication No. 91-3242; Chothia et al., (1987) *J. Mol. Biol.* 196:901-917; Chothia et al., (1989) *Nature* 342:877-883; and Al-Lazikani et al., (1997) *J. Mol. Biol.* 273:927-948; Tomlinson et al., (1992) *J. fol. Biol.* 227: 776-798; and Cox et al., (1994) *Eur. J. Immunol.* 24:827-836; the contents of each of which are expressly incorporated herein by reference.

Bispecific Molecules and Multivalent Antibodies

In another aspect, the present disclosure features biparatopic, bispecific, multispecific or polyspecific molecules comprising a MIF-binding antigen binding moiety and a D-DT binding antigen binding moiety. In another aspect, the present disclosure features biparatopic, bispecific, multispecific or polyspecific molecules comprising a MIF-binding antigen binding moiety and a D-DT binding antigen binding moiety wherein said MIF-binding antigen binding moiety and said D-DT binding antigen binding moiety are not identical.

In another aspect, the present disclosure features biparatopic, bispecific, multispecific or polyspecific molecules comprising an MIF-binding antibody and a D-DT binding antibody, or fragments thereof. In another aspect, the present disclosure features biparatopic, bispecific, multispecific or polyspecific molecules comprising a MIF-binding antibody and a D-DT binding antibody, or fragments thereof, wherein said MIF-binding antibody and D-DT binding antibody comprise antigen binding moieties which are not identical. In another aspect the present disclosure features a bispecific antigen binding moiety that specifically binds to MIF and D-DT. In another aspect the bispecific antigen binding moiety, is selected from the group consisting of a bispecific-scFv, a tetravalent bispecific antibody, a cross-linked Fab or a bispecific IgG.

In another aspect, the present disclosure provides multivalent compounds comprising at least two identical or different antigen-binding moieties derived from MIF/D-DT cross-reactive antibodies.

In another aspect, the present disclosure provides multivalent compounds comprising at least two different antigen-binding moieties wherein one of said antigen-binding moiety specifically binds to MIF and a second said antigen-binding moiety binds to D-DT and wherein said antigen-binding moieties can be linked together via protein fusion or covalent or non covalent linkage.

Tetravalent compounds can be obtained for example by cross-linking antibodies of the antibodies of the disclosure with an antibody that binds to the constant regions of the antibodies of the disclosure, for example the Fc or hinge region. Trimerizing domain are described for example in Borean patent EP 1012280B1. Pentamerizing modules are described for example in PCT/EP97/05897.

An antibody of the disclosure, or the antigen-binding regions thereof, can be linked to another functional molecule, e.g., another peptide or protein (e.g., another antibody or ligand for a receptor) to generate a bispecific molecule that binds to at least two different binding sites or target molecules.

To create a bispecific molecule of the disclosure, an antibody can be functionally linked (e.g., by chemical coupling, genetic fusion, non-covalent association or otherwise) to one or more other binding molecules, such as another antibody, antibody fragment, peptide or binding mimetic, such that a bispecific molecule results.

The bispecific molecules of the present disclosure can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl) cyclohaxane-1-carboxylate (sulfo-SMCC) (see e.g., Karpovsky et al., (1984) *J. Exp. Med.* 160: 1686; Liu et al. (1985) *Proc. Natl. Acad. Sci. USA* 82:8648). Other methods include those described in Paulus (1985) *Behring Ins. Mitt. No.* 78:118-132; Brennan et al., (1985) *Science* 229:81-83), and Glennie et al., (1987) *J. Immunol.* 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAbxmAb, mAbxFab, FabxF (ab')$_2$ or ligandx Fab fusion protein. A bispecific molecule of the disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Further clinical benefits may be provided by the binding of two or more antigens within one antibody (Morrison et al., (1997) *Nature Biotech.* 15:159-163; Alt et al. (1999) *FEBS Letters* 454: 90-94; Zuo et al., (2000) *Protein Engineering* 13:361-367; Lu et al., (2004) *JBC* 279:2856-2865; Lu et al., (2005) *JBC* 280:19665-19672; Marvin et al., (2005) *Acta Pharmacologica Sinica* 26:649-658; Marvin et al., (2006) *Curr Opin Drug Disc Develop* 9:184-193; Shen et al., (2007) *J Immun Methods* 218:65-74; Wu et al., (2007) *Nat Biotechnol.* 11:1290-1297; Dimasi et al., (2009) *J Mol Biol.* 393:672-692; and Michaelson et al., (2009) *mAbs* 1:128-141.

Binding of the bispecific or cross-reactive molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of antigen-antibody complexes of particular interest by employing a labeled reagent (e.g., an antibody) specific for the complex of interest.

Scaffolds

Other antibody/immunoglobulin frameworks or scaffolds comprising "antigen-binding moieties" can be employed in line with the present disclosure. This includes non-immunoglobulin based antibodies and scaffolds onto which CDRs of the disclosure can be grafted.

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and lama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the disclosure using standard cloning techniques.

Camelid antibody proteins obtained from members of the camel and dromedary (Camelus bactrianus and Calelus dromaderius) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See WO1994/04678.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies; they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris Brassicae has been used to develop anticalins by mutagenizing the set of four loops. One example of a patent application describing anticalins is in PCT Publication No. WO1999/16873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO2001/04144 and examples of "ubiquitin-like" proteins are described in WO2004/106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

Generation of Antibodies (i) Nucleic Acids Encoding the Antibodies

The disclosure provides substantially purified nucleic acid molecules which encode polypeptides comprising segments or domains of the MIF/D-DT cross-reactive antibody chains described above. In a specific embodiment, the nucleic acid molecules are those identified in Table 1. Some other nucleic acid molecules of the disclosure comprise nucleotide sequences that are substantially identical (e.g., at least 65, 80%, 85%, 90%, 95%, or 99%) to the nucleotide sequences of those identified in Table 1. Subcloning of above mentioned nucleic acids into conventional and appropriate expression vectors and expression of said expression vectors in an appropriate expression system originates polypeptides encoded by these polynucleotides which are cross-reactive to MIF and D-DT.

Also provided in the disclosure are polynucleotides which encode at least one CDR region and usually all three CDR regions from the heavy or light chain of the MIF/D-DT cross-reactive antibody set forth above. Some other polynucleotides encode all or substantially all of the variable region sequence of the heavy chain and/or the light chain of the MIF/D-DT cross-reactive antibody set forth above. Because of the composition of the genetic code, a variety of nucleic acid sequences will encode each of the immunoglobulin amino acid sequences.

The polynucleotide sequences can be produced by de novo solid-phase DNA synthesis or by PCR mutagenesis of an existing sequence (e.g., sequences as described in the Examples below) encoding an MIF/D-DT cross-reactive antibody or its binding fragment. Direct chemical synthesis of nucleic acids can be accomplished by methods known in the art, such as the phosphotriester method of Narang et al., (1979) Meth. Enzymol. 68:90; the phosphodiester method of Brown et al., (1979) Meth. Enzymol. 68:109; the diethylphosphoramidite method of Beaucage et al., (1981) Tetra. Lett., 22:1859; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., (1991) Nucleic Acids Res. 19:967; and Eckert et al., (1991) PCR Methods and Applications 1:17.

Also provided in the disclosure are expression vectors and host cells for producing the MIF/D-DT cross-reactive antibodies described above. Various expression vectors can be employed to express the polynucleotides encoding the MIF/D-DT cross-reactive antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., (1997) Nat Genet 15:345). For example, nonviral vectors useful for expression of the MIF/D-DT cross-reactive polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., (1995) Annu. Rev. Microbiol. 49:807; and Rosenfeld et al., (1992) Cell 68:143.

The choice of expression vector depends on the intended host cells in which the vector is to be expressed. Typically, the expression vectors contain a promoter and other regulatory sequences (e.g., enhancers) that are operably linked to the polynucleotides encoding an MIF/D-DT cross-reactive antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an MIF/D-DT cross-reactive antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., (1994) Results Probl. Cell Differ. 20:125; and Bittner et al., (1987) *Meth. Enzymol.,* 153:516). For example, the SV40 enhancer or CMV enhancer may be used to increase expression in mammalian host cells.

The expression vectors may also provide a secretion signal sequence position to form a fusion protein with polypeptides encoded by inserted MIF/D-DT cross-reactive antibody sequences. More often, the inserted MIF/D-DT cross-reactive antibody sequences are linked to signal sequences before inclusion in the vector. Vectors to be used to receive sequences encoding MIF/D-DT cross-reactive antibody light and heavy chain variable domains may also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the MIF/D-DT cross-reactive antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other Enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express MIF/D-DT cross-reactive polypeptides of the disclosure. Insect cells in combination with baculovirus vectors can also be used.

In some preferred embodiments, mammalian host cells are used to express and produce the MIF/D-DT cross-reactive polypeptides of the present disclosure. For example, they can be either a hybridoma cell line expressing endogenous immunoglobulin genes or a mammalian cell line harboring an exogenous expression vector including any normal mortal or normal or abnormal immortal animal or human cell. (e.g., the SP2/0 myeloma cells, CHO cells, HeLa cells, PER.C6 cells, COS cells, HKB11 cells, NS0 cells). For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen et al., (1986) *Immunol. Rev.* 89:49-68), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation nucleic acid conjugates, naked DNA, artificial virions, fusion to the herpes virus structural protein VP22 (Elliot and O'Hare, (1997) *Cell* 88:223), agent-enhanced uptake of DNA, and ex vivo transduction. For long-term, high-yield production of recombinant proteins, stable expression will often be desired.

(ii) Generation of Monoclonal Antibodies

Monoclonal antibodies (mAbs) can be produced by a variety of techniques, including conventional monoclonal antibody methodology e.g., the standard somatic cell hybridization technique of Kohler and Milstein, (1975) *Nature* 256:495. Many techniques for producing monoclonal antibody can be employed e.g., viral or oncogenic transformation of B-lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g. human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter et al., and U.S. Pat. Nos. 5,530,101; 5,585,089; 5693762 and 6180370 to Queen et al.

In a certain embodiment, the antibodies of the disclosure are human monoclonal antibodies. Such human monoclonal antibodies can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg et al. (1994) *Handbook of Experimental Pharmacology* 113:49-101; Lonberg and Huszar, (1995) *Intern. Rev. Immunol.* 13: 65-93, and Harding and Lonberg, (1995) *Ann.*

N.Y. Acad. Sci. 764:536-546). The preparation and use of HuMAb mice, and the genomic modifications carried by such mice, is further described in Taylor et al., (1992) *Nucleic Acids Research* 20:6287-6295; Chen et al., (1993) *International Immunology* 5: 647-656; Tuaillon et al., (1993) *Proc. Natl. Acad. Sci. USA* 94:3720-3724; Choi et al., (1993) *Nature Genetics* 4:117-123; Chen et al., (1993) *EMBO J.* 12:821-830; Tuaillon et al., (1994) *J. Immunol.* 152:2912-2920; Taylor et al., (1994) *International Immunology* 579-591; and Fishwild et al., (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO1992/103918, WO1993/12227, WO1994/25585, WO1997/113852, WO1998/24884 and WO1999/45962, all to Lonberg and Kay; and PCT Publication No. WO2001/14424.

In another embodiment, human antibodies of the disclosure can be raised using a mouse that carries human immunoglobulin sequences on transgenes and transchromosomes such as a mouse that carries a human heavy chain transgene and a human light chain transchromosome. Such mice, referred to herein as "KM mice", are described in detail in PCT Publication WO2002/43478 to Ishida et al.

Still further, alternative transgenic animal systems expressing human immunoglobulin genes are available in the art and can be used to raise MIF/D-DT cross-reactive antibodies of the disclosure. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise MIF/D-DT cross-reactive antibodies of the disclosure. For example, mice carrying both a human heavy chain transchromosome and a human light chain transchromosome, referred to as "TC mice" can be used; such mice are described in Tomizuka et al., (2000) *Proc. Natl. Acad. Sci. USA* 97:722-727. Furthermore, cows carrying human heavy and light chain transchromosomes have been described in the art (Kuroiwa et al., (2002) *Nature Biotechnology* 20:889-894) and can be used to raise MIF/D-DT cross-reactive antibodies of the disclosure.

Human monoclonal antibodies of the disclosure can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the disclosure can also be prepared using ribosome display, m-RNA display, bacterial display and yeast display methods for screening libraries of human immunoglobulin genes. In general eukaryotic cells displaying human antibody libraries are standard in the art (see Plückthun, A. (1997) *Proc. Natl. Acad. Sci. U.S.A.* 94 (10): 4937-42; Lipovsek et al. (2004) *Imm. Methods* 290 (1-2): 51-67; He et al. (2007) *Nature* 4 (3): 281-288; Gold et al. (2001) *Proc Natl Acad Sci USA* 98 (9): 4825-6; Fukuda I, Kojoh K, Tabata N, et al. (2006) *Nucleic Acids Res.* 34 (19): e127; Francisco et al. (1993) *Proc. Nat. Acad. Sci. U.S.A.* 90: 10444-48; Georgiou et al. (1997) *Nat. Biotech.* 15 (1): 29-34; Boder et al. (2000) *Proc Nat Acad Sci,* 97 (20):10701-10705; Weaver-Feldhaus et al. (2004) *FEBS Letters* 564 (1-2): 24-34).

Human monoclonal antibodies of the disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

(iii) Framework or Fc Engineering

One type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. The corresponding modified isotype version is known as IgG1f LALA in the scientific community. As already mentioned above, this approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO1994/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO2000/42072 by Presta. Moreover, the binding sites on human IgG1 for FcγRl, FcγRII, FcγRIII and FcRn have been mapped and variants with improved binding have been described (see Shields et al., (2001) *J. Biol. Chem.* 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO2003/035835 by Presta describes a variant CHO cell line, Lec13 cells, with reduced ability to attach fucose to Asn(297)-linked carbohydrates, also resulting in hypofucosylation of antibodies expressed in that host cell (see also Shields et al., (2002) *J. Biol. Chem.* 277:26733-26740). PCT Publication WO1999/54342 by Umana et al. describes cell lines engineered to express glycoprotein-modifying glycosyl transferases (e.g., beta (1,4)-N acetylglucosaminyl transferase III (GnTIII)) such that antibodies expressed in the engineered cell lines exhibit increased bisecting GlcNac structures which results in increased ADCC activity of the antibodies (see also Umana et al., (1999) *Nat. Biotech.* 17:176-180).

In another embodiment, the antibody is modified to increase its biological half-life. Various approaches are possible. For example, one or more of the following mutations can be introduced: T252L, T254S, and T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

Pharmaceutical Compositions

The disclosure provides pharmaceutical compositions comprising the MIF/D-DT cross-reactive antigen-binding moieties (intact or binding fragments) formulated together with a pharmaceutically acceptable carrier. In one embodiment of the disclosure the MIF/D-DT cross-reactive antibody (intact or binding fragments) is formulated together with a pharmaceutically acceptable carrier. The compositions can additionally contain one or more other therapeutic agents that are suitable for treating or preventing MIF and/or D-DT related diseases. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present disclosure can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antigen-binding moiety, antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the disclosure can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the MIF/D-DT cross-reactive antigen-binding moiety is employed in the pharmaceutical compositions of the disclosure. MIF/D-DT cross-reactive antigen-binding moieties are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parental compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the disclosure employed in the pharmaceutical composition at levels lower than that required to achieve the desired therapeutic effect and gradually increase the dosage until the desired effect is achieved. In general, effective doses of the compositions of the present disclosure, for the treatment of an allergic inflammatory disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. An exemplary treatment regime entails systemic administration once per every two weeks or once a month or once every 3 to 6 months. For intravitreal administration with an antibody, the dosage ranges from about 0.0001 to about 10 mg. An exemplary treatment regime entails systemic administration once per every two weeks or once a month or once every 3 to 6 months.

The Antigen-binding moieties and antibodies of the present disclosure are usually administered on multiple occasions. Intervals between single dosages can be weekly, monthly or yearly. In some methods of systemic administration, dosage is adjusted to achieve a plasma antibody concentration of 1-1000 µg/ml and in some methods 25-500 µg/ml. Alternatively the antigen-binding moiety can be administered as a sustained release formulation, in which case less frequent administration is required. Dosage and frequency vary depending on the half-life of the antigen-binding moiety in the patient. In general, human and humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

To prepare pharmaceutical or sterile compositions including MIF/D-DT cross-reactive antibody (intact or binding fragments), the MIF/D-DT cross-reactive antibody (intact or binding fragments) is mixed with a pharmaceutically acceptable carrier or excipient.

The desired dose of antibodies or fragments thereof is about the same as for an antibody or polypeptide, on a moles/ kg body weight basis. The desired plasma concentration of the antibodies or fragments thereof is about, on a moles/kg body weight basis. The dose may be at least 15 µg at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For antibodies or fragments thereof of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the antibodies or fragments thereof of the disclosure may be calculated using the patient's weight in kilograms (kg) multiplied by the dose to be administered in mg/kg. The dosage of the antibodies or fragments thereof of the disclosure may be 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a patient's body weight.

Unit dose of the antibodies or fragments thereof of the disclosure may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the antibodies or fragments thereof of the disclosure may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in a subject. Alternatively, the dosage of the antibodies or fragments thereof of the disclosure may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of antibodies or fragments thereof of the disclosure may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side affects (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al. (1983) Biopolymers 22:547-556; Langer, et al. (1981) J. Biomed. Mater. Res. 15:167-277; Langer (1982) Chem. Tech. 12:98-105; Epstein, et al. (1985) Proc. Natl. Acad. Sci. USA 82:3688-3692; Hwang, et al. (1980) Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO1992/19244, WO1997/32572, WO1997/44013, WO1998/31346, and WO1999/66903, each of which is incorporated herein by reference their entirety.

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies or fragments thereof of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

Additional therapies (e.g., prophylactic or therapeutic agents), which can be administered in combination with the antibodies or fragments thereof of the disclosure may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies or fragments thereof of the disclosure. The two or more therapies may be administered within one same patient visit.

The antibodies or fragments thereof of the disclosure and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the antibodies or fragments thereof of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p 120 (Schreier et al (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The disclosure provides protocols for the administration of pharmaceutical composition comprising antibodies or fragments thereof of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof of the disclosure are administered to a subject in a sequence and within a time interval such that the antibodies of the disclosure can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

The disclosure having been fully described, it is further illustrated by the following examples and claims, which are illustrative and are not meant to be further limiting.

TABLE 1

Antibody sequences

| SEQ ID NUMBER | Ab region | Sequence |
|---|---|---|
| (A) MOR014093 | | |
| SEQ ID NO: 1 (Kabat) | HCDR1 | DYYMD |
| SEQ ID NO: 2 (Kabat) | HCDR2 | AISSSGSTTYYADSVKG |
| SEQ ID NO: 3 (Kabat) | HCDR3 | GNLFGSTYVMGFDH |
| SEQ ID NO: 4 (Kabat) | LCDR1 | SGDSIGSTHVS |
| SEQ ID NO: 5 (Kabat) | LCDR2 | RKSNRPS |
| SEQ ID NO: 6 (Kabat) | LCDR3 | SSWDSESVV |
| SEQ ID NO: 7 (Chothia) | HCDR1 | GFTFSDY |
| SEQ ID NO: 8 (Chothia) | HCDR2 | SSSGST |
| SEQ ID NO: 9 (Chothia) | HCDR3 | GNLFGSTYVMGFDH |
| SEQ ID NO: 10 (Chothia) | LCDR1 | SGDSIGSTHVS |
| SEQ ID NO: 11 (Chothia) | LCDR2 | RKSNRPS |
| SEQ ID NO: 12 (Chothia) | LCDR3 | SSWDSESVV |
| SEQ ID NO: 13 | VL | DIELTQPPSVSVSPGQTASITCSGDSIG-STHVSWYQQKPGQAPVLVIYRKSNRPSGIPE RFSGSNSGNTATLTISGTQAEDEADYYCSSWDSESVVFGGGTKLTVLGQ |
| SEQ ID NO: 14 | VH | QVQLLESGGGLVQPGGSLRLSCAASGFTFSDYYMDWVRQAPGKGLEWVSAISSSGS TTYYADSVKGRFTISRDNSKNTLYLQMNSLRAEDTAVYYCARGNLFGSTYVMGFDH WGQGTLVTVSS |
| SEQ ID NO: 15 | DNA VL | GATATCGAACTGACCCAGCCGCCGAGCGTGAGCGTGAGCCCGGGCCAGACCGCG AGCATTACCTGTAGCGGCGATTCCATCGGTTCTACTCATGTTTCTTGGTACCAGCA GAAACCGGGCCAGGCGCCGGTGCTGGTGATCTACCGTAAATCTAACCGTCCGAG CGGCATCCCGGAACGTTTTAGCGGATCCAACAGCGGCAACACCGCGACCCTGACC ATTAGCGGCACCCAGGCGGAAGACGAAGCGGATTATTACTGCTCTTCTTGGGACT CTGAATCTGTTGTGTTTGGCGGCGGCACGAAGTTAACCGTCCTAGGTCAG |
| SEQ ID NO: 16 | DNA VH | CAGGTGCAATTGCTGGAAAGCGGCGGTGGCCTGGTGCAGCCGGGTGGCAGCCT GCGTCTGAGCTGCGCGGCGTCCGGATTCACCTTTTCTGACTACTACATGGACTGG GTGCGCCAGGCCCCGGGCAAAGGTCTCGAGTGGGTTTCCGCTATCTCTTCTTCTG |

TABLE 1-continued

Antibody sequences

| SEQ ID NUMBER | Ab region | Sequence |
|---|---|---|
| | | GTTCTACTACCTACTATGCGGATAGCGTGAAAGGCCGCTTTACCATCAGCCGCGA
TAATTCGAAAAACACCCTGTATCTGCAAATGAACAGCCTGCGTGCGGAAGATACG
GCCGTGTATTATTGCGCGCGTGGTAACCTGTTCGGTTCTACTTACGTTATGGGTTT
CGATCATTGGGGCCAAGGCACCCTGGTGACTGTTAGCTCA |

(B) MOR014116

| SEQ ID NUMBER | Ab region | Sequence |
|---|---|---|
| SEQ ID NO: 17 (Kabat) | HCDR1 | DYAIS |
| SEQ ID NO: 18 (Kabat) | HCDR2 | LIIPLFGTANYAQKFQG |
| SEQ ID NO: 19 (Kabat) | HCDR3 | SPAYQLVTPYYYVSDWFDV |
| SEQ ID NO: 20 (Kabat) | LCDR1 | SGSSSNIGSNYVS |
| SEQ ID NO: 21 (Kabat) | LCDR2 | DNSERPS |
| SEQ ID NO: 22 (Kabat) | LCDR3 | QSWDASPWSYV |
| SEQ ID NO: 23 (Chothia) | HCDR1 | GGTFSDY |
| SEQ ID NO: 24 (Chothia) | HCDR2 | IPLFGT |
| SEQ ID NO: 25 (Chothia) | HCDR3 | SPAYQLVTPYYYCSDWFDV |
| SEQ ID NO: 26 (Chothia) | LCDR1 | SGSSSNIGSNYVS |
| SEQ ID NO: 27 (Chothia) | LCDR2 | DNSERPS |
| SEQ ID NO: 28 (Chothia) | LCDR3 | QSWDASPWSYV |
| SEQ ID NO: 29 | VL | DIVLTQPPSVSGAPGQRVTISCSGSSS-
NIGSNYVSWYQQLPGTAPKLLIYDNSERPSGV
PDRFSGSKSGTSASLAITGLQAEDEADYYCQSWDASPWSYVFGGGTKLTVLGQ |
| SEQ ID NO: 30 | VH | QVQLVQSGAEVKKPGSSVKVSCKASGGTFSDYAISWVRQAPGQGLEWMGLIIPLFG
TANYAQKFQGRVTITADESTSTAYMELSSLRSEDTAVYYCARSPAYQLVTPYYYVSDW
FDVWGQGTLVTVSS |
| SEQ ID NO: 31 | DNA VL | GATATCGTGCTGACCCAGCCGCCGAGCGTGAGCGGTGCACCGGGCCAGCGCGTG
ACCATTAGCTGTAGCGGCAGCAGCAGCAACATTGGTTCTAACTACGTGTCTTGGT
ACCAGCAGCTGCCGGGCACGGCGCCGAAACTGCTGATCTACGACAACTCTGAAC
GCCCGAGCGGCGTGCCGGATCGCTTTAGCGGATCCAAAAGCGGCACCAGCGCCA
GCCTGGCGATTACCGGCCTGCAAGCAGAAGACGAAGCGGATTATTACTGCCAGT
CTTGGGACGCTTCTCCGTGGTCTTACGTGTTTGGCGGCGGCACGAAGTTAACCGT
CCTAGGTCAG |
| SEQ ID NO: 32 | DNA VH | CAGGTGCAATTGGTGCAGAGCGGTGCCGAAGTGAAAAAACCGGGCAGCAGCGT
GAAAGTTAGCTGCAAAGCATCCGGAGGGACGTTTTCTGACTACGCTATCTCTTGG
GTGCGCCAGGCCCCGGGCCAGGGCTCGAGTGGATGGGCCTGATCATCCCGCTG
TTCGGCACTGCGAACTACGCCCAGAAATTTCAGGGCCGGGTGACCATTACCGCCG
ATGAAAGCACCAGCACCGCCTATATGGAACTGAGCAGCCTGCGCAGCGAAGATA
CGGCCGTGTATTATTGCGCGCGTTCTCCGGCTTACCAGCTGGTTACTCCGTACTAC
TACGTTTCTGACTGGTTCGATGTTTGGGGCCAAGGCACCCTGGTGACTGTTAGCTCA |

(C) MOR014138

| SEQ ID NUMBER | Ab region | Sequence |
|---|---|---|
| SEQ ID NO: 33 (Kabat) | HCDR1 | SYAIH |

TABLE 1-continued

Antibody sequences

| SEQ ID NUMBER | Ab region | Sequence |
|---|---|---|
| SEQ ID NO: 34 (Kabat) | HCDR2 | RIIPHFGTAYYAQKFQG |
| SEQ ID NO: 35 (Kabat) | HCDR3 | VQVYMSVLGWGYENYMDV |
| SEQ ID NO: 36 (Kabat) | LCDR1 | RASQSVSAFQLG |
| SEQ ID NO: 37 (Kabat) | LCDR2 | GASTRAT |
| SEQ ID NO: 38 (Kabat) | LCDR3 | QQYIQYPYT |
| SEQ ID NO: 39 (Chothia) | HCDR1 | GGTFTSY |
| SEQ ID NO: 40 (Chothia) | HCDR2 | IPHFGT |
| SEQ ID NO: 41 (Chothia) | HCDR3 | VQVYMSVLGWGYENYMDV |
| SEQ ID NO: 42 (Chothia) | LCDR1 | RASQSVSAFQLG |
| SEQ ID NO: 43 (Chothia) | LCDR2 | GASTRAT |
| SEQ ID NO: 44 (Chothia) | LCDR3 | QQYIQYPYT |
| SEQ ID NO: 45 | VL | DIVLTQSPATLSLSPGERATLSCRASQS-VSAFQLGWYQQKPGQAPRLLIYGASTRATGIPARFSGSGSGTDFTLTISSLEPEDFAVYYCQQYIQYPYTFGQGTKVEIKRT |
| SEQ ID NO: 46 | VH | QVQLVQSGAEVKKPGSSVKVSCKASGGTFTSYAIHWVRQAPGQGLEWMFRIIPHFGTAYYAQKFQGRVTITADESTSTAYMELSSLRSEDTAVYYCARVQVYMSVLGWGYENYMDVWGQGTLVTVSS |
| SEQ ID NO: 47 | DNA VL | GATATCGTGCTGACCCAGAGCCCGGCGACCCTGAGCCTGAGCCCGGGTGAACGTGCCACCCTGAGCTGCAGAGCGAGCCAGTCTGTTTCTGCTTTCCAGCTGGGTTGGTACCAGCAGAAACCGGGCCAGGCCCCGCGTCTATTAATCTACGGTGCTTCTACTCGTGCGACCGGCATTCCGGCGCGTTTTAGCGGCAGCGGATCCGGCACCGATTTCACCCTGACCATTAGCAGCCTGGAACCGGAAGACTTTGCGGTGTATTATTGCCAGCAGTACATCCAGTACCCGTACACCTTTGGCCAGGGCACGAAAGTTGAATTAAACGTACG |
| SEQ ID NO: 48 | DNA VH | CAGGTGCAATTGGTGCAGAGCGGTGCCGAAGTGAAAAAACCGGGCAGCAGCGTGAAAGTTAGCTGCAAAGCATCCGGAGGGACGTTTACTTCTTACGCTATCCATTGGGTGCGCCAGGCCCCGGGCCAGGGCCTCGAGTGGATGGGCCGTATCATCCCGCATTTCGGCACTGCGTACTACGCCCAGAAATTTCAGGGCCGGGTGACCATTACCGCCGATGAAAGCACCAGCACCGCCTATATGGAACTGAGCAGCCTGCGCAGCGAAGATACGGCCGTGTATTATTGCGCGCGTGTTCAGGTTTACATGTCTGTTCTGGGTTGGGGTTACGAAAACTACATGGATGTTGGGGCCAAGGCACCCTGGTGACTGTTAGCTCA |

Material & Methods

The disclosure having been fully described, it is further illustrated by the following examples and claims, which are illustrative and are not meant to be further limiting.

I: Use of a Phage Display Antibody Library for the Identification of Antibodies

For the selection of antibodies cross-specifically recognizing MIF and D-DT a commercially available phage display library, the MorphoSys HuCAL PLATINUM® library was used. Therapeutic antibodies cross-specific for MIF and D-DT were generated by identification and selection of clones having binding affinities to both proteins. Said antibody library is based on the HuCAL® concept (Knappik et al., (2000) J Mol Biol 296:57-86) and employs the CysDisplay™ technology for displaying the Fab on the phage surface (WO2001/05950 to Lohning).

(a) Panning

To identify MIF/D-DT cross-reactive antibodies various panning strategies had been performed throughout the project. Thereby recombinant, purified human MIF and human D-DT were used as panning antigens. Recombinant MIF refers to MIF as defined in Accession No.: CAG30406.1 D-DT refers to D-DT as defined in Accession No. NP_001346. Both antigens had been used as un-tagged, HIS-tagged or biotinylated antigens for the selection and screening process.

All described panning strategies and antigens were used for the antibody selection process. Each panning strategy comprised of at least 3 individual rounds of panning and contained unique antigens, antigen concentrations and washing stringency. Furthermore all described panning strategies and antigens were combined and mixed and used as various differential panning strategies.

i) Solid Phase Panning Against MIF and D-DT

For solid phase pannings, blocked phages were incubated with recombinant MIF or D-DT protein coated on a solid surface (e.g. Maxisorp plate) or recombinant biotinylated MIF or D-DT immobilized on a reacti-bind neutravidin plate (Thermo Scientifc). Unspecific phages were washed away extensively by using PBST and PBS. At least 3 rounds of panning were performed and the antigens MIF or D-DT were used either consistently throughout the 3 rounds of panning or in an alternating manner.

Upon each round of panning the remaining phages were eluted, and eluted phages were used immediately for infection of *E. coli* TG1 bacteria. After rescue of the phages by using helper phage the polyclonal amplified phage output was titered again and used in consecutive selection steps.

For each individual panning the antigen concentration and the washing stringency were adjusted according to the output titers determined after each individual panning round to drive the selection for clones bearing high affinitiy to respective antigen.

(ii) Polyclonal Anti-MIF Antibody Capture Panning Against MIF

Furthermore a polyclonal MIF-specific antiserum was used to present purified MIF protein on a solid surface to the phage library for panning purposes. Thereby the polyclonal MIF-specific antibody was coated on a maxisorp plate O/N. After washing with PBS and blocking with 5% milk/PBS purified MIF protein was subjected to the plate and was further incubated for 1 hour. Thereby MIF was captured by the coated MIF-specific antibodies and was presented to the phages in various orientations. At least 3 rounds of panning were performed according to the description in solid phase panning against MIF and D-DT.

(iii) Semi-Solution Panning Against MIF and D-DT

For semi-solution pannings, recombinant human MIF was linked to carboxylic acid M-270-Dynabeads.

Pre-cleared phages were incubated for 1-2 hours with MIF-coated beads on a rotator. Beads were then collected using a magnetic separator and washed with PBST and PBS. Bead-bound phages were eluted for 7 min at RT in 300 µL 10 mM Tris-HCl/20 mM DTT, pH8.0. The eluted phages were used immediately for infection of *E. coli* TG1 bacteria. Phage infection, amplification, phage production and output titer determination were conducted as described above in solid phase panning against MIF and D-DT.

(iv) Solution Phase Panning Against Biotinylated MIF and D-DT

Each round of solution phase panning was performed using various biotinylated recombinant MIF or biotinylated recombinant D-DT proteins. Proteins were biotinylated using Amersham ECL™ Protein Biotinylation kit (GE Healthcare) according to the manufacturer's instructions. Streptavidin linked magnetic beads (Dynabeads, Dynal) and HuCAL PLATINUM® phage-antibodies were washed and blocked with Chemiblocker (Chemicon). The phage supernatant was transferred to a blocked 2 mL reaction tube and the appropriate biotinylated antigen was added and incubated for 60 minutes at room temperature on a rotator. 100 µl of blocked Streptavidin magnetic beads were added to each panning pool and the mixture incubated for 20 minutes on a room temperature rotator. The beads were collected with a magnetic particle separator (Dynal) for approximately 3 minutes and the solution discarded. Background binding phages were removed by extensive washing using PBST. Bound phage were eluted from the Dynabeads by adding 200 µl 20 mM DTT/10 mM Tris-HCl (pH 8) to each tube and incubating at room temperature for 15 minutes. Dynabeads were removed using the magnetic particle separator and the supernatant were subjected to *E. coli* TG-1. Additional phages were collected from the Dynabeads by mixing once with 200 µl PBS, collecting the supernatant and adding to *E. coli* TG-1 as previously described. Phage infection was performed in an identical manner to that described in solid phase panning.

(v) Solution Phase Panning Against Non-biotinylated MIF-His

As biotinylation might have a negative influence on the natural 3-dimensional structure of MIF an alternative solution phase panning strategy was included additionally. The panning process was in general as described above but to allow the use of non-biotinylated MIF-molecules the His tag of the phage-MIF-His complex was captured by Ni-NTA magnetic beads.

(b) Subcloning and Microexpression of Selected Fab Fragments

To facilitate rapid expression of soluble Fab, the Fab encoding inserts of the selected HuCAL PLATINUM® phage were subcloned via restriction enzyme cutting sites into specific expression vectors. After transformation of TG1-F bacteria using the Fab-encoding vectors single clone expression and preparation of periplasmic extracts containing HuCAL®-Fab fragments were performed. Fab-containing periplasmic extracts were used for the initial screening steps.

For secondary screening steps purified Fabs had been used. Expression of Fab fragments in TG-1 cells was carried out in shaker flask cultures using 500 ml of 2×YT medium supplemented with 34 µg/ml chloramphenicol. Cultures were shaken at 30° C. until the $OD_{600nm}$ reached 0.5. Expression was induced by addition of 0.75 mM IPTG for 20 h at 30° C. Cells were disrupted using lysozyme and Fab fragments isolated by Ni-NTA chromatography (Bio-Rad, Germany). Protein concentrations were determined by UV-spectrophotometry. Purity of Fab fragments was analyzed in denatured, reduced state using SDS-PAGE and in native state by HP-SEC.

2: Conversion to IgG

In order to express full length IgGs, variable domain fragments of heavy (VH) and light chains (VL) were subcloned from Fab expression vectors into appropriate pMORPH®_hIg vectors for human IgG2, human IgG4, human IgG4_Pro, and human IgG1f LALA.

3: Transient Expression and Purification of Human IgG

Eukaryotic HKB11 cells were transfected with equal amounts of IgG heavy and light chain expression vector (pMORPH2) or expression vector DNA encoding for heavy and light chains of IgGs (pMORPH4). The cell culture supernatant was generally harvested from 3 to 7 days post transfection. After sterile filtration, the solution was subjected to standard protein A affinity chromatography (MabSelect SURE, GE Healthcare). If not otherwise stated, buffer exchange was performed either to 1× Dulbecco's PBS (pH 7.2, Invitrogen) or to citrate buffer (100 mM citrate, 150 mM NaCl, pH 5.0) and samples were sterile filtered (0.2 µm pore size). Protein concentrations were determined by UV-spectrophotometry. Purity of IgG was analyzed under denaturing, reducing and non-reducing conditions in SDS-PAGE or by using Agilent BioAnalyzer and in native state by HP-SEC.

4: Screening (i) ELISA Screening on MIF and D-DT

Altogether more than 50 individual panning approaches had been performed which ended up in more than 50 pools of phages that had been screened to confirm cross-specificity to MIF and D-DT and to identify unique antibody clones.

Primary screening was done by ELISA and biotinylated recombinant human MIF or D-DT with a concentration of 1 µg/ml coated on reacti-bind neutravidin plates (Thermo Scientific) for 1, 5 h at room temperature. Reacti-bind neutravidin plates had been pretreated with PBS/5% skim milk powder before.

After washing with PBST Fab-containing periplasmic extracts or purified IgGs were applied and incubated for 2 hours a room temperature.

After subsequent washing antigen-specific bound Fab or IgG were detected via AP-Goat-anti-human IgG Fc-γ fragment specific (Fa Jackson ImmunoResearch) secondary antibody and subsequent application of Attophos (Fa ROCHE).

Results:

Upon primary screening ~3000 hits out of ~27000 clones analyzed in total were identified to specifically bind to MIF or D-DT. From these 3000 primary hits 740 were subjected to sequence analysis and 410 clones could be identified as being unique. After further extensive screening of these 410 clones, only 3 proofed to be cross-reactive for MIF and D-DT in Fab and IgG format.

WORKING EXAMPLES

Example 1

Specific Binding of Antibodies to Recombinant MIF and D-DT by ELISA

Cross-reactivity of antibodies to human MIF and human D-DT was determined by ELISA. Biotinylated recombinant human MIF or D-DT with a concentration of 1 µg/ml were coated on reacti-bind neutravidin coated black 384-well plates (Thermo Scientifc) for 1, 5 h at room temperature. Reacti-bind neutravidin plates had been pretreated with PBS/ 5% skim milk powder before. After washing with PBST purified IgGs were applied in a concentration of 6.25 nM on a MIF or a D-DT coated plate respectively and incubated for 2 hours at room temperature. After subsequent washing antigen-specific bound IgG was detected via AP-Goat-anti-human IgG Fc-γ fragment specific (Fa Jackson ImmunoResearch) secondary antibody and application of Attophos (Fa ROCHE) according to the manufacturer's manual. Fluorescence intensity was measured via Tecan Reader GeniosPro and fluorescence intensity for the individual clones was compared to control antibody.

Results:

After extensive characterization 3 individual clones were successfully identified to be cross-reactive to human MIF and human D-DT. They showed cross-reactive binding with at least 5-fold signal intensity compared to the negative control for both antigens (FIG. 2). Notably, prior art monoclonal anti-MIF-antibodies IIID9, Bax69 and Bax94 (see PCT Publication WO2009/086920) together with MAB289 (R&D) and 2A10 (AbD Serotec) were tested under the same conditions detected only human MIF but not D-DT and were not cross-reactive.

Example 2

$EC_{50}$ Determination of MIF and D-DT Cross-reactive Antibodies by ELISA

For further characterization, the $EC_{50}$ concentration for each of the cross-reactive antibodies to MIF and to D-DT was determined based on the ELISA setting according to Example 1. Concentrations of each of the individual antibodies were titrated and 8 distinct concentrations from 0 nM to 166 nM were applied side by side on a plate coated with MIF and a plate coated with D-DT. Biotinylated recombinant human MIF or D-DT with a concentration of 1 µg/ml were coated on reacti-bind neutravidin coated black 384-well plates (Thermo Scientifc) for 1, 5 h at room temperature. Reacti-bind neutravidin plates had been pretreated with PBS/5% skim milk powder before. After washing with PBST purified IgGs were added to the MIF or D-DT coated plate respectively and incubated for 2 hours at room temperature. After subsequent washing antigen-specific bound IgG was detected via AP-Goat-anti-human IgG Fc-γ fragment specific (Fa Jackson ImmunoResearch) secondary antibody and application of Attophos (Fa ROCHE) according to the manufacturer's manual. Fluorescence intensity was measured via Tecan Reader GeniosPro and fluorescence intensity for the individual clones was plotted in a typical antibody titration curve. $EC_{50}$ values were determined with the program GraphPad Prism using non-linear regression analysis.

Figure 3:
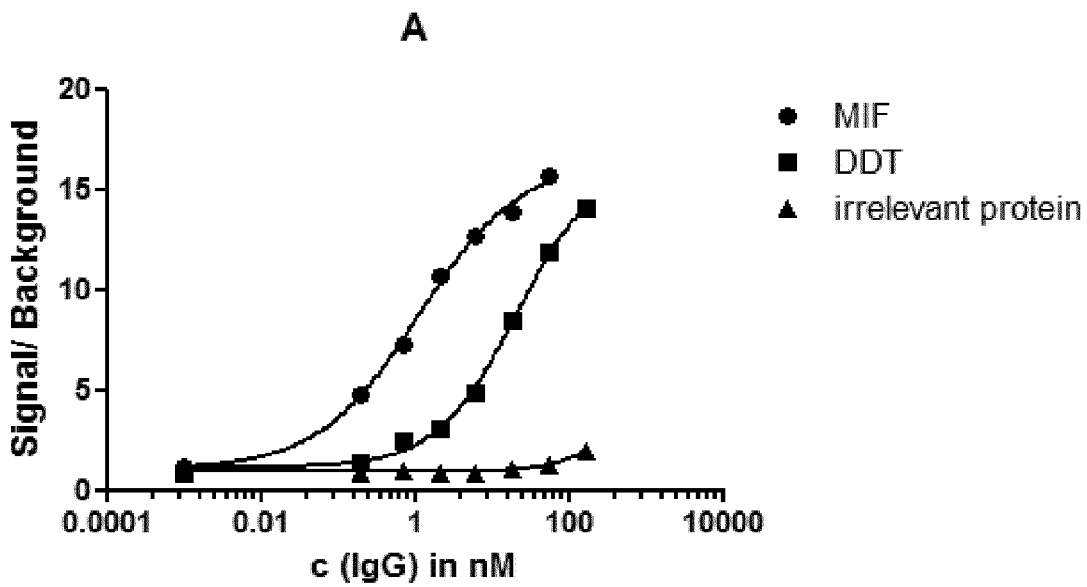
FIG. 3: Determination of $EC_{50}$ concentration ([nM]) of antibodies A and B to MIF and D-DT. (A=MOR014093; B=MOR014116)
Figure 3:
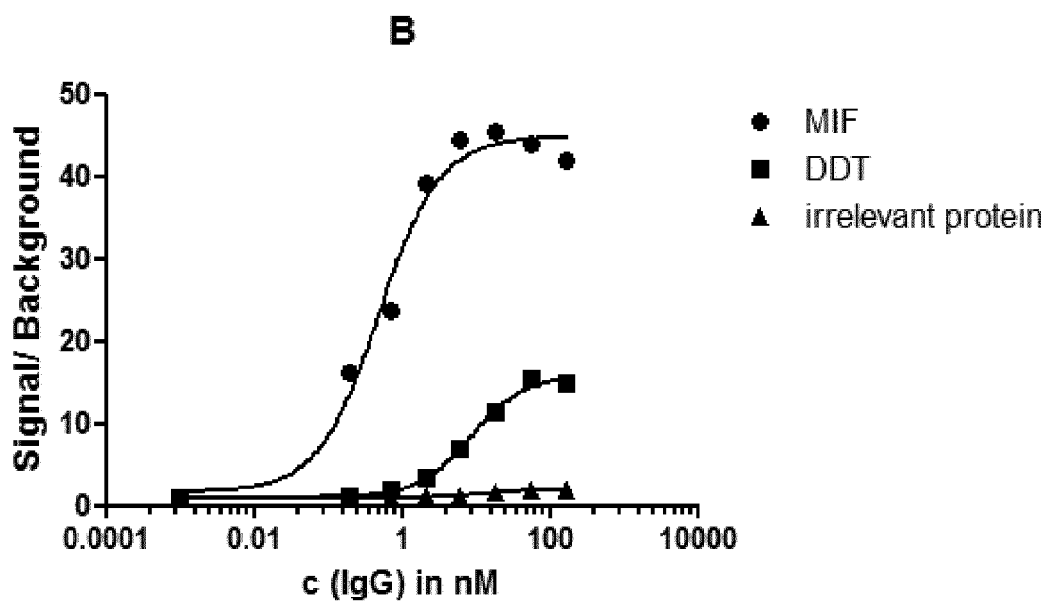
Figure 4:
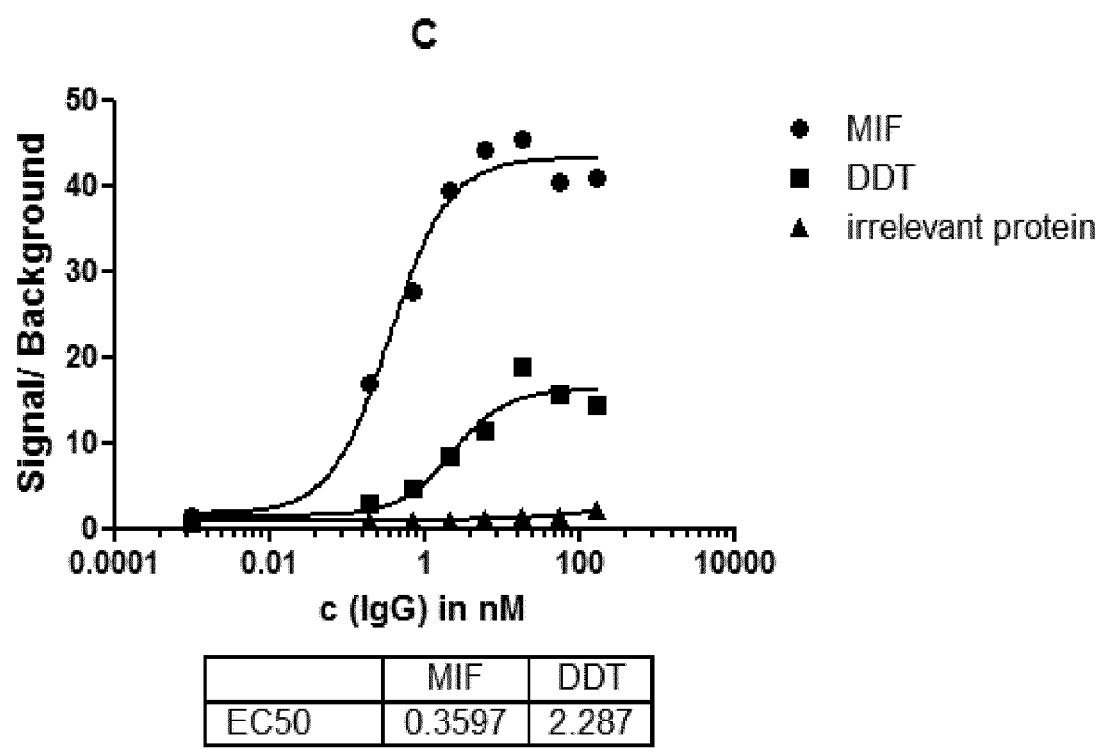
FIG. 4: Determination of $EC_{50}$ concentration ([nM]) of antibody C to MIF and D-DT. (C=MOR014138)

Results:

For all 3 MIF/D-DT cross-reactive antibodies (A=MOR014093; B=MOR014116; C=MOR014138) $EC_{50}$ concentration could have been determined and ranged from 0.3 nM to 22 nM (FIG. 3 and FIG. 4).

TABLE 2

$EC_{50}$ concentrations of MOR014093 (A), MOR014116 (B) and MOR014138 (C)

| Clone | $EC_{50}$ [nM] | |
|---|---|---|
| | MIF | D-DT |
| A | 1.138 | 21.24 |
| B | 0.486 | 8.473 |
| C | 0.3597 | 2.287 |

Example 3

Inhibition of MIF Binding to CD74 by MIF and D-DT Cross-reactive Antibodies

The ability of selected MIF and D-DT cross-reactive antibodies to inhibit binding of MIF to the receptor CD74 was analysed by an in vitro competition assay employing immobilized CD74 ectodomain ($sCD74^{73-232}$). Individual wells of a 384 well plate were coated O/N at 4° C. with 26 µg/ml $sCD74^{73-232}$, washed, and blocked for 2 h with PBS/5% BSA. Biotinylated MIF (5 µg/ml) in combination with anti-MIF/D-DT cross-reactive or control antibody (50 µg/ml) were co-applied in duplicates and incubated for two hours at room temperature. The bound, biotinylated MIF was determined by adding streptavidin-conjugated alkaline phosphatase for 1 h, followed by washing and detection with Attophos. Fluorescence intensity was measured via Tecan Reader GeniosPro. Values were plotted as percent fluorescence intensity relative to wells containing biotinylated human MIF with control antibody.

Figure 5:
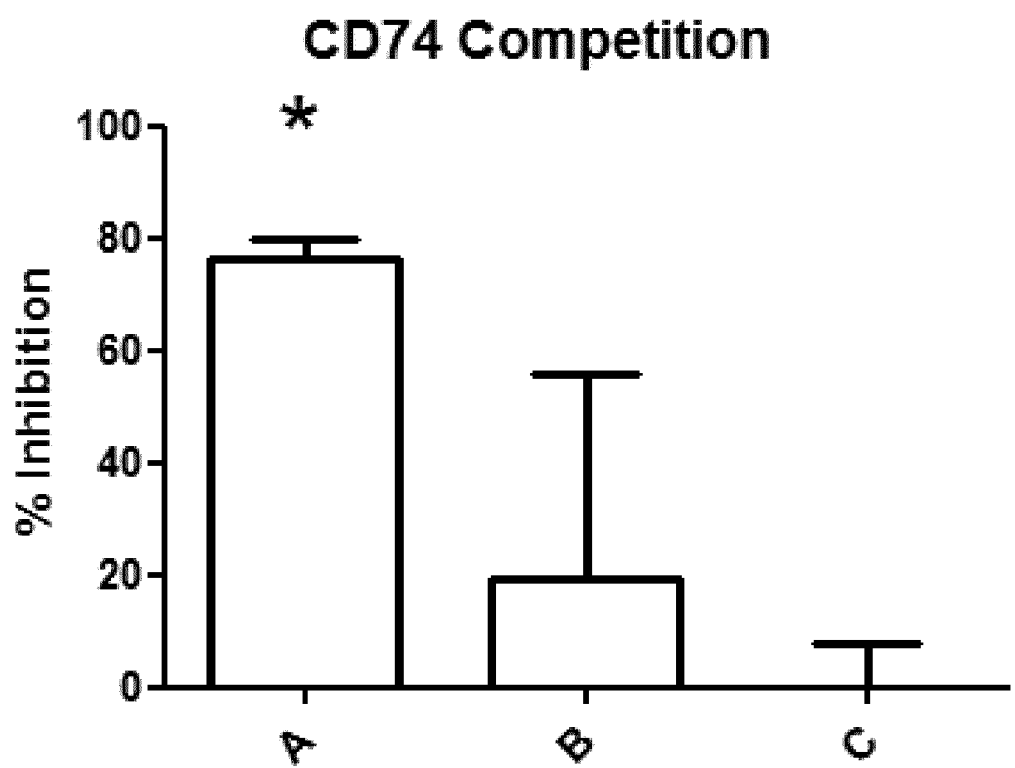
FIG. 5: Antibody-mediated inhibition of MIF and CD74 interaction. (A=MOR014093; B=MOR014116; C=MOR014138). *means statistically significant.

Taken together the MIF/D-DT cross-reactive antibodies disclosed in the present application showed different functionality in terms of inhibiting MIF-binding to CD74. While one antibody (MOR014093) turned out to inhibit almost 80% of MIF/CD74 interaction two antibodies (MOR014116 and MOR014138) showed moderate to absent inhibition of MIF-binding to CD74 (FIG. 5).

Example 4

Inhibition of IL-6 and IL-1β Release by MIF/D-DT Cross-reactive Antibodies

To further characterize MIF/D-DT cross-reactive antibodies release from IL-6 and IL-1β from monocytes was analyzed in presence of the 3 identified cross-specific antibodies.

Therefore peripheral blood mononuclear cells (PBMCs) had been isolated from donor blood according to standard protocol using Biocoll (Biochrome). Separation of monocytes from PBMCs was performed using the "human monocytes isolation kit II" from Miltenyi Biotec which is an indirect magnetic labelling system. Magnetic separation was done on a Vario MACS™ (Magnetic activated cell sorting; Miltenyi Biotec) separator with LS columns according to the instructor's manual.

Isolated monocytes (~0.2×10$^6$ cells/ml; in RPMI medium containing 2% FCS) were transferred to a 96-well plate and were incubated with specific MIF/D-DT cross-reactive antibodies having a final concentration of 100 µg/ml per well for 1 hour at 37° C., 5% $CO_2$. Subsequently, antibody-treated monocytes were challenged with 0.1 ng/ml Escherichia coli (Serotype 0111:B4 O111:B4) LPS (Sigma) and incubated overnight at 37° C., 5% $CO_2$. Supernatants were collected and respective IL-6 and IL-1β concentration were determined via the bead-based CBA Flex Set system (BD Biosciences) and compared to unspecific antibody used as negative control.

Figure 6:
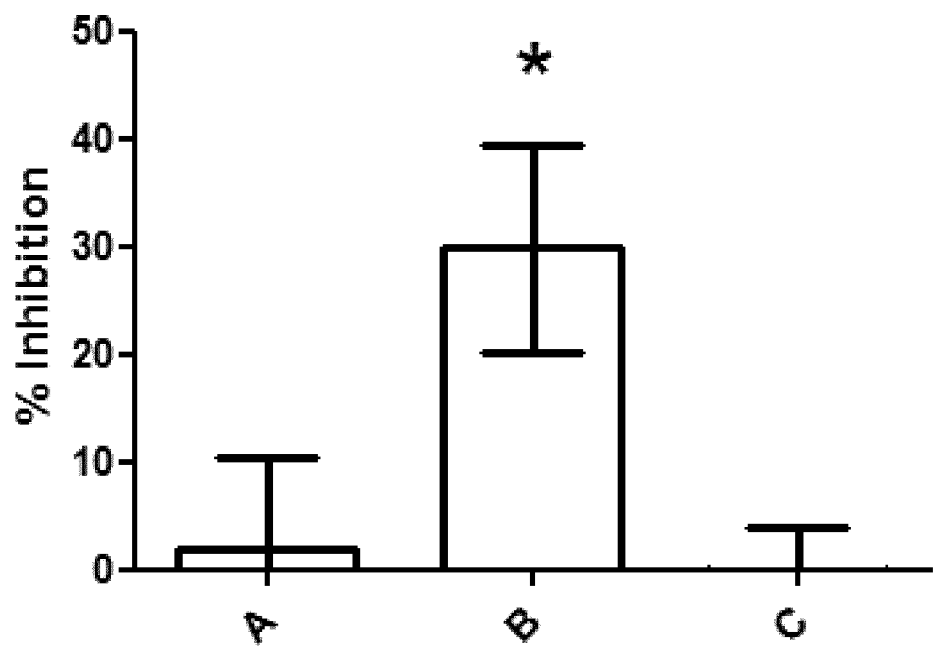
FIG. 6: Antibody-mediated inhibition of IL-1.beta. and IL-6 release from isolated human monocytes challenge with MIF and LPS. (A=MOR014093; B=MOR014116; C=MOR014138). *means statistically significant.
Figure 6:
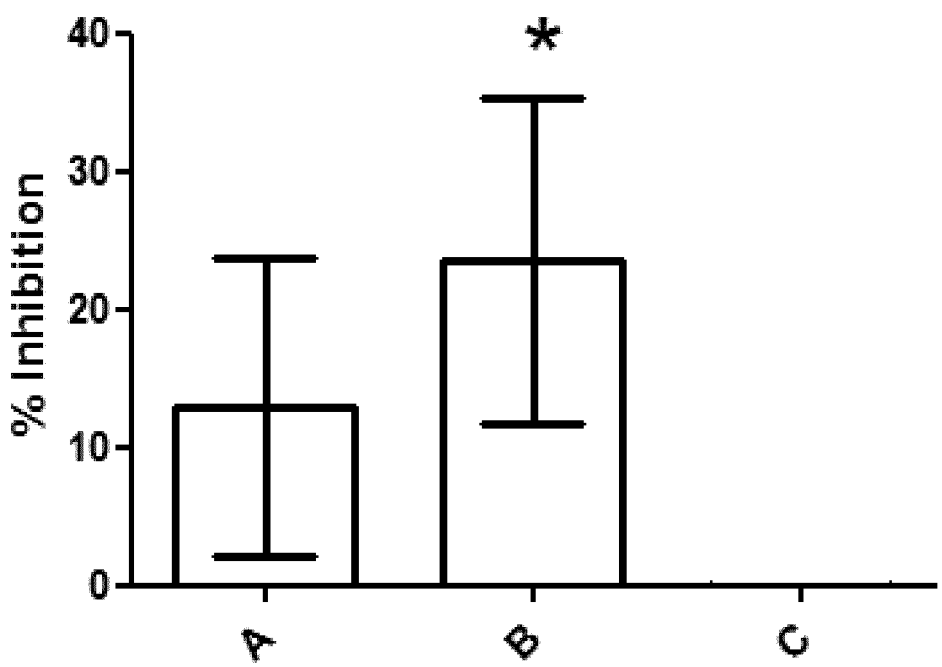

Upon analysis according to the description above antibody MOR014116 (B) retained 20% to 30% of IL-6 an IL-1β release induced upon LPS challenge while antibody MOR014093 (A) inhibited 10% of IL-1β and antibody MOR014138 (C) showed no effect for both pro-inflammatory cytokine analyzed (FIG. 6).

Example 5

Selection Strategy for the Identification of MIF/D-DT Cross-reactive Antibodies

For the identification of MIF/D-DT cross-reactive antibodies from a phage display antibody library a solution phase panning using recombinant human MIF and recombinant human D-DT as antigen in an alternating manner can be performed. By using MIF and D-DT in an alternating fashion throughout a three step panning procedure only antigen binding moieties detecting specific regions which are conserved in both antigens are identified.

Both antigens, the recombinant, purified human MIF and human D-DT, are used as biotinylated antigens for the selection and screening process and its functional activity is tested beforehand via a tautomerase assay as described below to ensure correct folding and physiological 3D structure of both proteins.

Tautomerase Activity Assay:

MIF as well as D-DT have an enzymatic activity (tautomerase) activity. This enzymatic active region is believed to be essential for their biological activity. The substrate Hydroxyphenylpyrimidine (HPP) is used. Alternatively D-Dopachrome can be used as substrate to analyze tautomerase activity. A MIF or D-DT containing solution is added to 3700 µl of Borate-Buffer and is supplemented with PBS to a total of 4000 µl for a final MIF or D-DT concentration of 50 nM. Thereof 96 µl are transferred to a 96-well plate. 4 µl of 25 mM 4-HPP (ALDRICH, Cat. #114286-5G, MW=180.16), pH 6.0 are added to respective wells and absorbance is read immediately at 306 nm for 30 seconds. Tautomerase activity for both proteins, MIF and D-DT, indicates its physiological conformation.

Alternating Solution Phase MIF-D-DT-MIF Panning Using Biotinylated Human MIF and Human D-DT Streptavidin linked magnetic beads (Dynabeads M-280, c=10 mg/ml, Dynal) and the phage preparation of a phage display antibody library are washed and blocked with Chemiblocker (Chemicon). Therefore 50 µl of each phage-antibodies preparation are mixed with 450 µl of PBS, and further 500 µl of 2× Chemiblocker/0.1% Tween are added. In parallel 1 ml of streptavidin linked magnetic beads are washed twice with 1 ml PBS and resuspended in 1 ml 1×Chemiblocker. After washing, beads are suspended in 100 µl PBS and 100 µl 1×Chemiblocker is added. Both, phages as well as magnetic beads are incubated for 1.5 h on a rotator at room temperature.

After chemi-blocking phage-antibodies preparations are incubated with streptavidin linked magnetic beads for 30 minutes to pre-adsorb all phage-antibodies that unspecifically stick to the magnetic beads. After incubation the beads are isolated using a magnetic separator and phage-containing supernatants are used for the first round of pannings.

1$^{st}$ Panning Round:

For the first panning round pre-blocked and pre-adsorbed phage-antibodies are added to 100 nM biotinylated human MIF and are incubated on a rotator for 1 h at room temperature. Afterwards the phage-antigen mixture are transferred to tubes containing the pre-blocked streptavidin linked magnetic beads and are incubated rotating for further 20 minutes before the magnetic beads are captured using a magnetic separator and the supernatant is carefully removed from the beads and discarded. Subsequently the remaining beads are washed 5× with 500 µl PBST without incubation, followed by 2 washing steps with PBST and 5 minutes incubation and rotation and 3 washing steps with PBS without incubation.

Phage Elution, Phage Infection and Phage Rescue:

After the last washing step the magnetic beads are resuspended in 200 µl 20 mM DTT/10 mM Tris-HCl (pH 8) elution buffer to elute the phages from the human MIF captured by the streptavidin linked magnetic beads. Then, isolated phages are transferred to a 50 ml Falcon tube containing pre-warmed E. coli TG-1$^+$ cultures and are incubated for 45 min at 37° C. without shaking to induce the phage infection of the E. coli bacteria.

After incubation the bacteria are isolated by centrifugation for 5 minutes, at 4000 g and 4° C. and the pellet is resuspended in 600 µl 2×YT medium and the bacterial suspension is plated onto 2 to 4 large LB/CAM/Glu agar plates. Plates are stored over night at 30° C.

On the next day bacteria are scraped off from the agar plates using 5 ml of 2×YT/Cam/Glu/glycerol (15%) and a sterile drygalski spatula and the suspension is either diluted to an $OD_{600nm}$ of ~0.4-0.5 or incubated at 37° C. until an $OD_{600nm}$ of ~0.4-0.5 is reached. 5 ml of the respective suspension are transferred to a separate tube and a VCSM13 helper phage preparation is added (totally 4.5×10$^{10}$ phages/5 ml culture) and incubated for 30 minutes at 37° C.

Afterwards the infected E. coli are centrifuged for 5 minutes at 4000 g and 4° C. and the supernatant is discarded. The pellet is resuspended in 20 ml of 2×YT/Cam/Kan/IPTG (0.25 nM) medium to induce the phage production in the absence of glucose. E. coli suspension is incubated for 18 h at 22° C. and shaking (250 rpm) and then centrifuged for 10 min at 4000 g and 4° C. The phage containing supernatant is collected and added to 5 ml of ice cold PEG/NaCl (20% PEG600, 2.5M NaCl) and incubated for 30 minutes on ice. The precipitated phages are isolated via centrifugation for 35 mM at 22000 g and 4° C. and the supernatant is discarded. The pellet of precipitated phage-antibodies is resuspended in 500 µl PBS and can be used for the next panning round.

2$^{nd}$ Panning Round:

For the 2nd panning round the output phages isolated from the first panning round are used and are incubated with 100 nM biotinylated human D-DT on a rotator for 1 h at room temperature. Afterwards the phage-antigen mixture are transferred to tubes containing the pre-blocked streptavidin linked magnetic beads and are incubated rotating for further 20 minutes before the magnetic beads are captured using a magnetic separator and the supernatant is carefully discarded. Subsequently the remaining beads are washed 5× with 500 µl PBST without incubation, followed by 3 washing steps with PBST and 5 minutes incubation and rotation and 3 washing steps with PBS without incubation.

After the 2$^{nd}$ round of panning the antigen-specific phages are eluted and isolated according to the description above.

3$^{rd}$ Panning Round:

For the 3rd panning round the output phages isolated from the 2$^{nd}$ panning round are used and are incubated with 10 nM biotinylated human MIF on a rotator for 1 h at room temperature. Afterwards the phage-antigen mixture are transferred to tubes containing the pre-blocked streptavidin linked magnetic beads and are incubated rotating for further 20 minutes before the magnetic beads are captured using a magnetic separator and the supernatant is carefully discarded. Subsequently the remaining beads are washed 5× with 500 µl PBST without incubation, followed by 3 washing steps with PBST and 10 minutes incubation and rotation and 3 washing steps with PBS without incubation.

After the 3$^{rd}$ round of panning the antigen-specific phages are eluted according to the description above and phage-DNA is isolated from infected bacteria and Fab-encoding DNA is subcloned into specific Fab-expression vectors as described in Material & Methods 1(b).

Isolated Fabs or IgGs after conversion can be screened and characterized according to the assay described herein.

Example 6

ELISA-based Cross-competition Assay

Cross-competition of an antibody or another binding agent that cross-reactively binds MIF and D-DT may be detected by using an ELISA assay according to the following standard procedure.

The general principle of the ELISA-assay involves coating an MIF/D-DT cross-reactive antibody onto the wells of an ELISA plate. An excess amount of a second, potentially cross-competitive, MIF/D-DT antibody is then added in solution (i.e. not bound to the ELISA plate). Subsequently a limited amount of MIF-Fc or D-DT-Fc is then added to the wells.

The antibody which is coated onto the wells and the antibody in solution will compete for binding of the limited number of MIF or D-DT molecules. The plate is then washed to remove MIF or D-DT molecules that have not bound to the coated antibody and to also remove the second, solution phase antibody as well as any complexes formed between the second solution phase antibody and MIF or D-DT. The amount of bound MIF or D-DT is then measured using an appropriate MIF or D-DT detection reagent. Therefore MIF or D-DT may be fused with a tag, like e.g. Fc, Flag, etc. which can be detected via an appropriate tag-specific antibody.

An antibody in solution that is cross-competitive to the coated antibody will be able to cause a decrease in the number of MIF or D-DT molecules that the coated antibody can bind relative to the number of MIF or D-DT molecules that the coated antibody can bind in the absence of the second, solution phase antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y MIF or D-DT binding sites per well are at least 10 fold higher than the moles of Ab-X MIF or D-DT binding sites that are used, per well, during the coating of the ELISA plate. MIF or D-DT is then added such that the moles of MIF or D-DT added per well were at least 25-fold lower than the moles of Ab-X MIF or D-DT binding sites that are used for coating each well. Following a suitable incubation period, the ELISA plate is washed and a MIF or D-DT detection reagent is added to measure the amount of MIF or D-DT molecules specifically bound by the coated MIF/D-DT cross-reactive antibody (in this case Ab-X). The background signal for the assay is defined as the signal obtained in wells with the coated antibody (in this case Ab-X), second solution phase antibody (in this case Ab-Y), buffer only (i.e. no MIF or D-DT) and MIF or D-DT detection reagents. The positive control signal for the assay is defined as the signal obtained in wells with the coated antibody (in this case Ab-X), second solution phase antibody buffer only (i.e. no second solution phase antibody), MIF or D-DT and MIF or D-DT detection reagents. The ELISA assay needs to be run in such a manner to have the positive control signal being at least 6 times the background signal.

To avoid any artifacts (e.g. significantly different affinities between Ab-X and Ab-Y for MIF or D-DT) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

The disclosure having been fully described, it is further illustrated by the following examples and claims, which are illustrative and are not meant to be further limiting.

Equivalents

The foregoing written specification is considered to be sufficient to enable one skilled in the art to practice the disclosure. The foregoing description and examples detail certain preferred embodiments of the disclosure and describe the best mode contemplated by the inventors. It will be appreciated, however, that no matter how detailed the foregoing may appear in text, the disclosure may be practiced in many ways and the disclosure should be construed in accordance with the appended claims and any equivalents thereof.

The invention claimed is:

1. An isolated antigen-binding moiety, wherein the antigen-binding moiety specifically binds human MIF and human D-DT,
   wherein the antigen-binding moiety recognizes an epitope of MIF,
   wherein a similar epitope is present in D-DT and
   wherein said isolated antigen-binding moiety recognizes both epitopes,
   said epitopes in MIF and D-DT comprise an amino acid shown in FIG. 1 that
   is identical in human MIF and human D-DT.

2. The isolated antigen-binding moiety of claim 1, wherein the isolated antigen-binding moiety binds to MIF and to D-DT with an $EC_{50}$ concentration of less than 100 nM.

3. The isolated antigen-binding moiety of claim 1, wherein the isolated antigen-binding moiety binds to MIF and to D-DT with a dissociation constant ($K_D$) of less than $1 \times 10^7$ $M^{-1}$.

4. The isolated antigen-binding moiety of claim 1, wherein the isolated antigen-binding moiety is an antibody, a fragment thereof, a single domain antibody, a maxibody, a minibody, an intrabody, a diabody, a triabody, a tetrabody, a v-NAR, a camelid antibody, or a domain antibody.

5. The antibody or fragment thereof of claim 4, wherein said antibody or fragment thereof is a monoclonal antibody or a polyclonal antibody.

6. The antibody or fragment thereof of claim 4, wherein said antibody is a human, humanized or chimeric antibody.

7. The antibody or fragment thereof of claim 4, wherein said antibody or fragment thereof is of the IgG isotype.

8. The antibody or fragment thereof of claim 4, wherein said antibody fragment thereof is selected from the group consisting of a Fab, F(ab2)', F(ab)2', scFV.

9. An antibody-derived scaffold comprising the antigen binding moiety of claim 1, wherein said antibody-derived scaffold is a bispecific antibody-derived scaffold selected from the group consisting of a bispecific-scFv, a tetravalent bispecific antibody, a cross-linked Fab or a bispecific IgG.

10. A pharmaceutical composition comprising an antigen binding moiety according to claim 1, and a pharmaceutically acceptable carrier.

11. An isolated antigen-binding moiety of claim 1 that cross-competes with an isolated antibody or fragment thereof, comprising heavy chain variable region CDR1 of SEQ ID NO: 1; CDR2 of SEQ ID NO: 2; CDR3 of SEQ ID NO: 3; and a light chain variable region CDR1 of SEQ ID NO: 4; CDR2 of SEQ ID NO: 5; and CDR3 of SEQ ID NO: 6.

12. An isolated antigen-binding moiety of claim 11 that binds to the same epitope as an isolated antibody or fragment thereof, comprising heavy chain variable region CDR1 of SEQ ID NO: 1; CDR2 of SEQ ID NO: 2; CDR3 of SEQ ID NO: 3; and a light chain variable region CDR1 of SEQ ID NO: 4; CDR2 of SEQ ID NO: 5; and CDR3 of SEQ ID NO: 6.

13. An isolated antigen-binding moiety of claim 1 that cross-competes with an isolated antibody or fragment thereof, comprising a heavy chain variable region CDR1 of SEQ ID NO: 17; CDR2 of SEQ ID NO: 18; CDR3 of SEQ ID NO: 19; and a light chain variable region CDR1 of SEQ ID NO: 20; CDR2 of SEQ ID NO: 21; and CDR3 of SEQ ID NO: 22.

14. An isolated antigen-binding moiety of claim 13 that binds to the same epitope as an isolated antibody or fragment thereof, comprising a heavy chain variable region CDR1 of SEQ ID NO: 17; CDR2 of SEQ ID NO: 18; CDR3 of SEQ ID NO: 19; and a light chain variable region CDR1 of SEQ ID NO: 20; CDR2 of SEQ ID NO: 21; and CDR3 of SEQ ID NO: 22.

15. An isolated antigen-binding moiety of claim 1 that cross-competes with an isolated antibody or fragment thereof, comprising a heavy chain variable region CDR1 of SEQ ID NO: 33; CDR2 of SEQ ID NO: 34; CDR3 of SEQ ID NO: 35; and a light chain variable region CDR1 of SEQ ID NO: 36; CDR2 of SEQ ID NO: 37; and CDR3 of SEQ ID NO: 38.

16. An isolated antigen-binding moiety of claim 15 that binds to the same epitope as an isolated antibody or fragment thereof, comprising a heavy chain variable region CDR1 of SEQ ID NO: 33; CDR2 of SEQ ID NO: 34; CDR3 of SEQ ID NO: 35; and a light chain variable region CDR1 of SEQ ID NO: 36; CDR2 of SEQ ID NO: 37; and CDR3 of SEQ ID NO: 38.

17. An isolated antigen-binding moiety of claim 1, comprising an antibody or fragment thereof having at least 95% sequence identity to an antibody or fragment thereof comprising the heavy chain variable region CDR1 of SEQ ID NO: 1; CDR2 of SEQ ID NO: 2; CDR3 of SEQ ID NO: 3; and a light chain variable region CDR1 of SEQ ID NO: 4; CDR2 of SEQ ID NO: 5; and CDR3 of SEQ ID NO: 6.

18. An isolated antibody or fragment thereof of claim 17, comprising a heavy chain variable region CDR1 of SEQ ID NO: 1; CDR2 of SEQ ID NO: 2; CDR3 of SEQ ID NO: 3; and a light chain variable region CDR1 of SEQ ID NO: 4; CDR2 of SEQ ID NO: 5; and CDR3 of SEQ ID NO: 6.

19. An isolated antibody or fragment thereof of claim 18 which antibody comprises a VH comprising SEQ ID NO: 14 and a VL comprising SEQ ID NO: 13.

20. An isolated antigen-binding moiety of claim 1, comprising an antibody or fragment thereof having at least 95% sequence identity to an antibody or fragment thereof comprising a heavy chain variable region CDR1 of SEQ ID NO: 17; CDR2 of SEQ ID NO: 18; CDR3 of SEQ ID NO: 19; and a light chain variable region CDR1 of SEQ ID NO: 20; CDR2 of SEQ ID NO: 21; and CDR3 of SEQ ID NO: 22.

21. An isolated antibody or fragment thereof of claim 20, comprising a heavy chain variable region CDR1 of SEQ ID NO: 17; CDR2 of SEQ ID NO: 18; CDR3 of SEQ ID NO: 19; and a light chain variable region CDR1 of SEQ ID NO: 20; CDR2 of SEQ ID NO: 21; and CDR3 of SEQ ID NO: 22.

22. An isolated antibody or fragment thereof of claim 21, which antibody comprises a VH comprising SEQ ID NO: 30 and a VL comprising SEQ ID NO: 29.

23. An isolated antigen-binding moiety of claim 1, comprising an antibody or fragment thereof having at least 95% sequence identity to an antibody or fragment thereof, comprising a heavy chain variable region CDR1 of SEQ ID NO: 33; CDR2 of SEQ ID NO: 34; CDR3 of SEQ ID NO: 35; and a light chain variable region CDR1 of SEQ ID NO: 36; CDR2 of SEQ ID NO: 37; and CDR3 of SEQ ID NO: 38.

24. An isolated antibody or fragment thereof of claim 23, comprising a heavy chain variable region CDR1 of SEQ ID NO: 33; CDR2 of SEQ ID NO: 34; CDR3 of SEQ ID NO: 35; and a light chain variable region CDR1 of SEQ ID NO: 36; CDR2 of SEQ ID NO: 37; and CDR3 of SEQ ID NO: 38.

25. An isolated antibody or fragment thereof of claim 24 which antibody comprises a VH comprising SEQ ID NO: 46 and a VL comprising SEQ ID NO: 45.

26. A nucleic acid encoding an isolated antigen-binding moiety according to claim 1.

27. A vector comprising a nucleic acid of claim 26.

28. An isolated host cell comprising a vector according to claim 27.

29. An isolated host cell according to claim 28 wherein the host cell is a mammalian cell.

30. An isolated host cell according to claim 28 wherein the host cell is a human cell.

31. A nucleic acid sequence encoding an isolated antigen-binding moiety according to claim 1, said antigen-binding moiety comprising an antibody or fragment thereof having at least 95% sequence identity to an antibody or fragment thereof encoded by the nucleic acids selected from the group consisting of
   1) SEQ ID NO: 15 encoding a variable light chain, and SEQ ID NO: 16 encoding a variable heavy chain;
   2) SEQ ID NO: 31 encoding a variable light chain, and SEQ ID NO: 32 encoding a variable heavy chain; and
   3) SEQ ID NO: 47 encoding a variable light chain, and SEQ ID NO: 48 encoding a variable heavy chain.

32. A nucleic acid encoding an isolated antibody or fragment thereof of claim 31, wherein the nucleic acid encoding the VH comprises SEQ ID NO: 16 and the nucleic acid encoding the VL comprises SEQ ID NO: 15.

33. A nucleic acid encoding an isolated antibody or fragment thereof of claim 31, wherein the nucleic acid encoding the VH comprises SEQ ID NO: 32 and the nucleic acid encoding the VL comprises SEQ ID NO: 31.

34. A nucleic acid encoding an isolated antibody or fragment thereof of claim 31, wherein the nucleic acid encoding the VH comprises SEQ ID NO: 48 and the nucleic acid encoding the VL comprises SEQ ID NO: 47.

* * * * *

SEQUENCE LISTING

<160> NUMBER OF SEQ ID NOS: 50

<210> SEQ ID NO 1
<211> LENGTH: 5
<212> TYPE: PRT
<213> ORGANISM: artificial sequences
<220> FEATURE:
<221> NAME/KEY: SOURCE
<222> LOCATION: 1..5
<223> OTHER INFORMATION: /mol_type="protein"
      /note="MOR014093_HCDR1 (Kabat)"
      /organism="artificial sequences"

<400> SEQUENCE: 1

Asp Tyr Tyr Met Asp
1               5

<210> SEQ ID NO 2
<211> LENGTH: 17
<212> TYPE: PRT
<213> ORGANISM: artificial sequences
<220> FEATURE:
<221> NAME/KEY: SOURCE
<222> LOCATION: 1..17
<223> OTHER INFORMATION: /mol_type="protein"
      /note="MOR014093_HCDR2 (Kabat)"
      /organism="artificial sequences"

<400> SEQUENCE: 2

Ala Ile Ser Ser Ser Gly Ser Thr Thr Tyr Tyr Ala Asp Ser Val Lys
1               5                   10                  15

Gly

<210> SEQ ID NO 3
<211> LENGTH: 14
<212> TYPE: PRT
<213> ORGANISM: artificial sequences
<220> FEATURE:
<221> NAME/KEY: SOURCE
<222> LOCATION: 1..14
<223> OTHER INFORMATION: /mol_type="protein"
      /note="MOR014093_HCDR3 (Kabat)"
      /organism="artificial sequences"

<400> SEQUENCE: 3

Gly Asn Leu Phe Gly Ser Thr Tyr Val Met Gly Phe Asp His
1               5                   10

<210> SEQ ID NO 4
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="MOR014093_LCDR1 (Kabat)"
      /organism="artificial sequences"

<400> SEQUENCE: 4

Ser Gly Asp Ser Ile Gly Ser Thr His Val Ser
1               5                   10

<210> SEQ ID NO 5
<211> LENGTH: 7
<212> TYPE: PRT
<213> ORGANISM: artificial sequences
<220> FEATURE:
<221> NAME/KEY: SOURCE

```
<222> LOCATION: 1..7
<223> OTHER INFORMATION: /mol_type="protein"
      /note="MOR014093_LCDR2 (Kabat)"
      /organism="artificial sequences"

<400> SEQUENCE: 5

Arg Lys Ser Asn Arg Pro Ser
1               5

<210> SEQ ID NO 6
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /mol_type="protein"
      /note="MOR014093_LCDR3 (Kabat)"
      /organism="artificial sequences"

<400> SEQUENCE: 6

Ser Ser Trp Asp Ser Glu Ser Val Val
1               5

<210> SEQ ID NO 7
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /mol_type="protein"
      /note="MOR014093_HCDR1 (Chotia)"
      /organism="artificial sequences"

<400> SEQUENCE: 7

Gly Phe Thr Phe Ser Asp Tyr
1               5

<210> SEQ ID NO 8
<211> LENGTH: 6
<212> TYPE: PRT
<213> ORGANISM: artificial sequences
<220> FEATURE:
<221> NAME/KEY: SOURCE
<222> LOCATION: 1..6
<223> OTHER INFORMATION: /mol_type="protein"
      /note="MOR014093_HCDR2 (Chotia)"
      /organism="artificial sequences"

<400> SEQUENCE: 8

Ser Ser Ser Gly Ser Thr
1               5

<210> SEQ ID NO 9
<211> LENGTH: 14
<212> TYPE: PRT
<213> ORGANISM: artificial sequences
<220> FEATURE:
<221> NAME/KEY: SOURCE
<222> LOCATION: 1..14
<223> OTHER INFORMATION: /mol_type="protein"
      /note="MOR014093_HCDR3 (Chotia)"
      /organism="artificial sequences"

<400> SEQUENCE: 9

Gly Asn Leu Phe Gly Ser Thr Tyr Val Met Gly Phe Asp His
1               5                   10
```

```
<210> SEQ ID NO 10
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="MOR014093_LCDR1 (Chotia)"
      /organism="artificial sequences"

<400> SEQUENCE: 10

Ser Gly Asp Ser Ile Gly Ser Thr His Val Ser
1               5                   10

<210> SEQ ID NO 11
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /mol_type="protein"
      /note="MOR014093_LCDR2 (Chotia)"
      /organism="artificial sequences"

<400> SEQUENCE: 11

Arg Lys Ser Asn Arg Pro Ser
1               5

<210> SEQ ID NO 12
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /mol_type="protein"
      /note="MOR014093_LCDR3 (Chotia)"
      /organism="artificial sequences"

<400> SEQUENCE: 12

Ser Ser Trp Asp Ser Glu Ser Val Val
1               5

<210> SEQ ID NO 13
<211> LENGTH: 108
<212> TYPE: PRT
<213> ORGANISM: artificial sequences
<220> FEATURE:
<221> NAME/KEY: SOURCE
<222> LOCATION: 1..108
<223> OTHER INFORMATION: /mol_type="protein"
      /note="MOR014093_VL"
      /organism="artificial sequences"

<400> SEQUENCE: 13

Asp Ile Glu Leu Thr Gln Pro Pro Ser Val Ser Val Ser Pro Gly Gln
1               5                   10                  15

Thr Ala Ser Ile Thr Cys Ser Gly Asp Ser Ile Gly Ser Thr His Val
            20                  25                  30

Ser Trp Tyr Gln Gln Lys Pro Gly Gln Ala Pro Val Leu Val Ile Tyr
        35                  40                  45

Arg Lys Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80
```

Asp Glu Ala Asp Tyr Tyr Cys Ser Ser Trp Asp Ser Glu Ser Val Val
            85                  90                  95

Phe Gly Gly Gly Thr Lys Leu Thr Val Leu Gly Gln
            100                 105

<210> SEQ ID NO 14
<211> LENGTH: 123
<212> TYPE: PRT
<213> ORGANISM: artificial sequences
<220> FEATURE:
<221> NAME/KEY: SOURCE
<222> LOCATION: 1..123
<223> OTHER INFORMATION: /mol_type="protein"
      /note="MOR014093_VH"
      /organism="artificial sequences"

<400> SEQUENCE: 14

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asp Trp Val Arg Gln Ala Pro Gly Lys Gly Leu Glu Trp Val
        35                  40                  45

Ser Ala Ile Ser Ser Ser Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Leu Phe Gly Ser Thr Tyr Val Met Gly Phe Asp His
            100                 105                 110

Trp Gly Gln Gly Thr Leu Val Thr Val Ser Ser
        115                 120

<210> SEQ ID NO 15
<211> LENGTH: 324
<212> TYPE: DNA
<213> ORGANISM: artificial sequences
<220> FEATURE:
<221> NAME/KEY: source
<222> LOCATION: 1..324
<223> OTHER INFORMATION: /mol_type="DNA"
      /note="MOR014093_DNA VL"
      /organism="artificial sequences"

<400> SEQUENCE: 15
gatatcgaac tgacccagcc gccgagcgtg agcgtgagcc cgggccagac cgcgagcatt      60
acctgtagcg gcgattccat cggttctact catgtttctt ggtaccagca gaaaccgggc     120
caggcgccgg tgctggtgat ctaccgtaaa tctaaccgtc cgagcggcat cccggaacgt     180
tttagcggat ccaacagcgg caacaccgcg accctgacca ttagcggcac ccaggcggaa     240
gacgaagcgg attattactg ctcttcttgg gactctgaat ctgttgtgtt tggcggcggc     300
acgaagttaa ccgtcctagg tcag                                            324

<210> SEQ ID NO 16
<211> LENGTH: 369
<212> TYPE: DNA
<213> ORGANISM: artificial sequences
<220> FEATURE:
<221> NAME/KEY: source
<222> LOCATION: 1..369
<223> OTHER INFORMATION: /mol_type="DNA"

/note="MOR014093 DNA VH"
/organism="artificial sequences"

<400> SEQUENCE: 16

| | |
|---|---|
| caggtgcaat tgctggaaag cggcggtggc ctggtgcagc cgggtggcag cctgcgtctg | 60 |
| agctgcgcgg cgtccggatt cacctttct gactactaca tggactgggt gcgccaggcc | 120 |
| ccgggcaaag gtctcgagtg ggtttccgct atctcttctt ctggttctac tacctactat | 180 |
| gcggatagcg tgaaaggccg ctttaccatc agccgcgata ttcgaaaaa caccctgtat | 240 |
| ctgcaaatga acagcctgcg tgcggaagat acggccgtgt attattgcgc gcgtggtaac | 300 |
| ctgttcggtt ctacttacgt tatgggtttc gatcattggg ccaaggcac cctggtgact | 360 |
| gttagctca | 369 |

<210> SEQ ID NO 17
<211> LENGTH: 5
<212> TYPE: PRT
<213> ORGANISM: artificial sequences
<220> FEATURE:
<221> NAME/KEY: SOURCE
<222> LOCATION: 1..5
<223> OTHER INFORMATION: /mol_type="protein"
    /note="MOR014116_HCDR1 (Kabat)"
    /organism="artificial sequences"

<400> SEQUENCE: 17

Asp Tyr Ala Ile Ser
1               5

<210> SEQ ID NO 18
<211> LENGTH: 17
<212> TYPE: PRT
<213> ORGANISM: artificial sequences
<220> FEATURE:
<221> NAME/KEY: SOURCE
<222> LOCATION: 1..17
<223> OTHER INFORMATION: /mol_type="protein"
    /note="MOR014116_HCDR2 (Kabat)"
    /organism="artificial sequences"

<400> SEQUENCE: 18

Leu Ile Ile Pro Leu Phe Gly Thr Ala Asn Tyr Ala Gln Lys Phe Gln
1               5                   10                  15
Gly

<210> SEQ ID NO 19
<211> LENGTH: 19
<212> TYPE: PRT
<213> ORGANISM: artificial sequences
<220> FEATURE:
<221> NAME/KEY: SOURCE
<222> LOCATION: 1..19
<223> OTHER INFORMATION: /mol_type="protein"
    /note="MOR014116_HCDR3 (Kabat)"
    /organism="artificial sequences"

<400> SEQUENCE: 19

Ser Pro Ala Tyr Gln Leu Val Thr Pro Tyr Tyr Tyr Val Ser Asp Trp
1               5                   10                  15
Phe Asp Val

<210> SEQ ID NO 20
<211> LENGTH: 13
<212> TYPE: PRT
<213> ORGANISM: artificial sequences

```
<220> FEATURE:
<221> NAME/KEY: SOURCE
<222> LOCATION: 1..13
<223> OTHER INFORMATION: /mol_type="protein"
      /note="MOR014116_LCDR1 (Kabat)"
      /organism="artificial sequences"

<400> SEQUENCE: 20

Ser Gly Ser Ser Ser Asn Ile Gly Ser Asn Tyr Val Ser
1               5                   10

<210> SEQ ID NO 21
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /mol_type="protein"
      /note="MOR014116_LCDR2 (Kabat)"
      /organism="artificial sequences"

<400> SEQUENCE: 21

Asp Asn Ser Glu Arg Pro Ser
1               5

<210> SEQ ID NO 22
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="MOR014116_LCDR3 (Kabat)"
      /organism="artificial sequences"

<400> SEQUENCE: 22

Gln Ser Trp Asp Ala Ser Pro Trp Ser Tyr Val
1               5                   10

<210> SEQ ID NO 23
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /mol_type="protein"
      /note="MOR014116_HCDR1 (Chotia)"
      /organism="artificial sequences"

<400> SEQUENCE: 23

Gly Gly Thr Phe Ser Asp Tyr
1               5

<210> SEQ ID NO 24
<211> LENGTH: 6
<212> TYPE: PRT
<213> ORGANISM: artificial sequences
<220> FEATURE:
<221> NAME/KEY: SOURCE
<222> LOCATION: 1..6
<223> OTHER INFORMATION: /mol_type="protein"
      /note="MOR014116_HCDR2 (Chotia)"
      /organism="artificial sequences"

<400> SEQUENCE: 24

Ile Pro Leu Phe Gly Thr
1               5
```

```
<210> SEQ ID NO 25
<211> LENGTH: 19
<212> TYPE: PRT
<213> ORGANISM: artificial sequences
<220> FEATURE:
<221> NAME/KEY: SOURCE
<222> LOCATION: 1..19
<223> OTHER INFORMATION: /mol_type="protein"
      /note="MOR014116_HCDR3 (Chotia)"
      /organism="artificial sequences"

<400> SEQUENCE: 25

Ser Pro Ala Tyr Gln Leu Val Thr Pro Tyr Tyr Tyr Val Ser Asp Trp
1               5                   10                  15

Phe Asp Val

<210> SEQ ID NO 26
<211> LENGTH: 13
<212> TYPE: PRT
<213> ORGANISM: artificial sequences
<220> FEATURE:
<221> NAME/KEY: SOURCE
<222> LOCATION: 1..13
<223> OTHER INFORMATION: /mol_type="protein"
      /note="MOR014116_LCDR1 (Chotia)"
      /organism="artificial sequences"

<400> SEQUENCE: 26

Ser Gly Ser Ser Ser Asn Ile Gly Ser Asn Tyr Val Ser
1               5                   10

<210> SEQ ID NO 27
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /mol_type="protein"
      /note="MOR014116_LCDR2 (Chotia)"
      /organism="artificial sequences"

<400> SEQUENCE: 27

Asp Asn Ser Glu Arg Pro Ser
1               5

<210> SEQ ID NO 28
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="MOR014116_LCDR3 (Chotia)"
      /organism="artificial sequences"

<400> SEQUENCE: 28

Gln Ser Trp Asp Ala Ser Pro Trp Ser Tyr Val
1               5                   10

<210> SEQ ID NO 29
<211> LENGTH: 112
<212> TYPE: PRT
<213> ORGANISM: artificial sequences
<220> FEATURE:
<221> NAME/KEY: SOURCE
<222> LOCATION: 1..112
```

<223> OTHER INFORMATION: /mol_type="protein"
/note="MOR014116 VL"
/organism="artificial sequences"

<400> SEQUENCE: 29

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Ser Glu Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Ala Ser Pro
                85                  90                  95

Trp Ser Tyr Val Phe Gly Gly Gly Thr Lys Leu Thr Val Leu Gly Gln
            100                 105                 110
```

<210> SEQ ID NO 30
<211> LENGTH: 128
<212> TYPE: PRT
<213> ORGANISM: artificial sequences
<220> FEATURE:
<221> NAME/KEY: SOURCE
<222> LOCATION: 1..128
<223> OTHER INFORMATION: /mol_type="protein"
/note="MOR014116 VH"
/organism="artificial sequences"

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Leu Ile Ile Pro Leu Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Ala Tyr Gln Leu Val Thr Pro Tyr Tyr Val Ser
            100                 105                 110

Asp Trp Phe Asp Val Trp Gly Gln Gly Thr Leu Val Thr Val Ser Ser
        115                 120                 125
```

<210> SEQ ID NO 31
<211> LENGTH: 336
<212> TYPE: DNA
<213> ORGANISM: artificial sequences
<220> FEATURE:
<221> NAME/KEY: source
<222> LOCATION: 1..336
<223> OTHER INFORMATION: /mol_type="DNA"
/note="MOR014116 DNA VL"
/organism="artificial sequences"

<400> SEQUENCE: 31

```
gatatcgtgc tgacccagcc gccgagcgtg agcggtgcac cgggccagcg cgtgaccatt      60
agctgtagcg gcagcagcag caacattggt tctaactacg tgtcttggta ccagcagctg     120
ccgggcacgg cgccgaaact gctgatctac gacaactctg aacgcccgag cggcgtgccg     180
gatcgcttta gcggatccaa aagcggcacc agcgccagcc tggcgattac cggcctgcaa     240
gcagaagacg aagcggatta ttactgccag tcttgggacg cttctccgtg gtcttacgtg     300
tttggcggcg gcacgaagtt aaccgtccta ggtcag                               336
```

```
<210> SEQ ID NO 32
<211> LENGTH: 384
<212> TYPE: DNA
<213> ORGANISM: artificial sequences
<220> FEATURE:
<221> NAME/KEY: source
<222> LOCATION: 1..384
<223> OTHER INFORMATION: /mol_type="DNA"
      /note="MOR014116 DNA VH"
      /organism="artificial sequences"

<400> SEQUENCE: 32
```

```
caggtgcaat tggtgcagag cggtgccgaa gtgaaaaaac cgggcagcag cgtgaaagtt      60
agctgcaaag catccggagg gacgtttttct gactacgcta tctcttgggt gcgccaggcc    120
ccgggccagg gcctcgagtg gatgggcctg atcatcccgc tgttcggcac tgcgaactac     180
gcccagaaat tcagggccgg ggtgaccatt accgccgatg aaagcaccag caccgcctat     240
atggaactga gcagcctgcg cagcgaagat acggccgtgt attattgcgc gcgttctccg     300
gcttaccagc tggttactcc gtactactac gtttctgact ggttcgatgt ttggggccaa     360
ggcaccctgg tgactgttag ctca                                             384
```

```
<210> SEQ ID NO 33
<211> LENGTH: 5
<212> TYPE: PRT
<213> ORGANISM: artificial sequences
<220> FEATURE:
<221> NAME/KEY: SOURCE
<222> LOCATION: 1..5
<223> OTHER INFORMATION: /mol_type="protein"
      /note="MOR014138_HCDR1 (Kabat)"
      /organism="artificial sequences"

<400> SEQUENCE: 33

Ser Tyr Ala Ile His
1               5
```

```
<210> SEQ ID NO 34
<211> LENGTH: 17
<212> TYPE: PRT
<213> ORGANISM: artificial sequences
<220> FEATURE:
<221> NAME/KEY: SOURCE
<222> LOCATION: 1..17
<223> OTHER INFORMATION: /mol_type="protein"
      /note="MOR014138_HCDR2 (Kabat)"
      /organism="artificial sequences"

<400> SEQUENCE: 34

Arg Ile Ile Pro His Phe Gly Thr Ala Tyr Tyr Ala Gln Lys Phe Gln
1               5                   10                  15

Gly
```

```
<210> SEQ ID NO 35
<211> LENGTH: 18
```

```
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
      /note="MOR014138_HCDR3 (Kabat)"
      /organism="artificial sequences"

<400> SEQUENCE: 35

Val Gln Val Tyr Met Ser Val Leu Gly Trp Gly Tyr Glu Asn Tyr Met
1               5                   10                  15
Asp Val

<210> SEQ ID NO 36
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="MOR014138_LCDR1 (Kabat)"
      /organism="artificial sequences"

<400> SEQUENCE: 36

Arg Ala Ser Gln Ser Val Ser Ala Phe Gln Leu Gly
1               5                   10

<210> SEQ ID NO 37
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /mol_type="protein"
      /note="MOR014138_LCDR2 (Kabat)"
      /organism="artificial sequences"

<400> SEQUENCE: 37

Gly Ala Ser Thr Arg Ala Thr
1               5

<210> SEQ ID NO 38
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /mol_type="protein"
      /note="MOR014138_LCDR3 (Kabat)"
      /organism="artificial sequences"

<400> SEQUENCE: 38

Gln Gln Tyr Ile Gln Tyr Pro Tyr Thr
1               5

<210> SEQ ID NO 39
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /mol_type="protein"
      /note="MOR014138_HCDR1 (Chotia)"
      /organism="artificial sequences"
```

```
<400> SEQUENCE: 39

Gly Gly Thr Phe Thr Ser Tyr
1               5

<210> SEQ ID NO 40
<211> LENGTH: 6
<212> TYPE: PRT
<213> ORGANISM: artificial sequences
<220> FEATURE:
<221> NAME/KEY: SOURCE
<222> LOCATION: 1..6
<223> OTHER INFORMATION: /mol_type="protein"
      /note="MOR014138_HCDR2 (Chotia)"
      /organism="artificial sequences"

<400> SEQUENCE: 40

Ile Pro His Phe Gly Thr
1               5

<210> SEQ ID NO 41
<211> LENGTH: 18
<212> TYPE: PRT
<213> ORGANISM: artificial sequences
<220> FEATURE:
<221> NAME/KEY: SOURCE
<222> LOCATION: 1..18
<223> OTHER INFORMATION: /mol_type="protein"
      /note="MOR014138_HCDR3 (Chotia)"
      /organism="artificial sequences"

<400> SEQUENCE: 41

Val Gln Val Tyr Met Ser Val Leu Gly Trp Gly Tyr Glu Asn Tyr Met
1               5                   10                  15

Asp Val

<210> SEQ ID NO 42
<211> LENGTH: 12
<212> TYPE: PRT
<213> ORGANISM: artificial sequences
<220> FEATURE:
<221> NAME/KEY: SOURCE
<222> LOCATION: 1..12
<223> OTHER INFORMATION: /mol_type="protein"
      /note="MOR014138_LCDR1 (Chotia)"
      /organism="artificial sequences"

<400> SEQUENCE: 42

Arg Ala Ser Gln Ser Val Ser Ala Phe Gln Leu Gly
1               5                   10

<210> SEQ ID NO 43
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /mol_type="protein"
      /note="MOR014138_LCDR2 (Chotia)"
      /organism="artificial sequences"

<400> SEQUENCE: 43

Gly Ala Ser Thr Arg Ala Thr
1               5

<210> SEQ ID NO 44
<211> LENGTH: 9
<212> TYPE: PRT
```

<213> ORGANISM: artificial sequences
<220> FEATURE:
<221> NAME/KEY: SOURCE
<222> LOCATION: 1..9
<223> OTHER INFORMATION: /mol_type="protein"
    /note="MOR014138_LCDR3 (Chotia)"
    /organism="artificial sequences"

<400> SEQUENCE: 44

Gln Gln Tyr Ile Gln Tyr Pro Tyr Thr
1               5

<210> SEQ ID NO 45
<211> LENGTH: 110
<212> TYPE: PRT
<213> ORGANISM: artificial sequences
<220> FEATURE:
<221> NAME/KEY: SOURCE
<222> LOCATION: 1..110
<223> OTHER INFORMATION: /mol_type="protein"
    /note="MOR014138 VL"
    /organism="artificial sequences"

<400> SEQUENCE: 45

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ala Phe
                20                  25                  30

Gln Leu Gly Trp Tyr Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ile Gln Tyr Pro
                85                  90                  95

Tyr Thr Phe Gly Gln Gly Thr Lys Val Glu Ile Lys Arg Thr
            100                 105                 110

<210> SEQ ID NO 46
<211> LENGTH: 127
<212> TYPE: PRT
<213> ORGANISM: artificial sequences
<220> FEATURE:
<221> NAME/KEY: SOURCE
<222> LOCATION: 1..127
<223> OTHER INFORMATION: /mol_type="protein"
    /note="MOR014138 VH"
    /organism="artificial sequences"

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
                20                  25                  30

Ala Ile His Trp Val Arg Gln Ala Pro Gly Gln Gly Leu Glu Trp Met
        35                  40                  45

Gly Arg Ile Ile Pro His Phe Gly Thr Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gln Val Tyr Met Ser Val Leu Gly Trp Gly Tyr Glu Asn
            100                 105                 110

Tyr Met Asp Val Trp Gly Gln Gly Thr Leu Val Thr Val Ser Ser
        115                 120                 125

<210> SEQ ID NO 47
<211> LENGTH: 330
<212> TYPE: DNA
<213> ORGANISM: artificial sequences
<220> FEATURE:
<221> NAME/KEY: source
<222> LOCATION: 1..330
<223> OTHER INFORMATION: /mol_type="DNA"
      /note="MOR014138 DNA VL"
      /organism="artificial sequences"

<400> SEQUENCE: 47
gatatcgtgc tgacccagag cccggcgacc ctgagcctga gcccgggtga acgtgccacc    60
ctgagctgca gcgagcca gtctgtttct gctttccagc tgggttggta ccagcagaaa    120
ccgggccagg ccccgcgtct attaatctac ggtgcttcta ctcgtgcgac cggcattccg    180
gcgcgtttta gcggcagcgg atccggcacc gatttcaccc tgaccattag cagcctggaa    240
ccggaagact ttgcggtgta ttattgccag cagtacatcc agtacccgta cacctttggc    300
cagggcacga agttgaaat taaacgtacg    330

<210> SEQ ID NO 48
<211> LENGTH: 381
<212> TYPE: DNA
<213> ORGANISM: artificial sequences
<220> FEATURE:
<221> NAME/KEY: source
<222> LOCATION: 1..381
<223> OTHER INFORMATION: /mol_type="DNA"
      /note="MOR014138 DNA VH"
      /organism="artificial sequences"

<400> SEQUENCE: 48
caggtgcaat tggtgcagag cggtgccgaa gtgaaaaaac cgggcagcag cgtgaaagtt    60
agctgcaaag catccggagg gacgtttact tcttacgcta tccattgggt gcgccaggcc    120
ccgggccagg gcctcgagtg gatgggccgt atcatcccgc atttcggcac tgcgtactac    180
gcccagaaat tcagggccg ggtgaccatt accgccgatg aaagcaccag caccgcctat    240
atggaactga gcagcctgcg cagcgaagat acggccgtgt attattgcgc gcgtgttcag    300
gtttacatgt ctgttctggg ttggggttac gaaaactaca tggatgtttg gggccaaggc    360
accctggtga ctgttagctc a    381

<210> SEQ ID NO 49
<211> LENGTH: 115
<212> TYPE: PRT
<213> ORGANISM: Homo sapiens
<220> FEATURE:
<221> NAME/KEY: SOURCE
<222> LOCATION: 1..115
<223> OTHER INFORMATION: /mol_type="protein"
      /note="MIF; Accession No.: CAG30406.1"
      /organism="Homo sapiens"

<400> SEQUENCE: 49

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly

```
                        20                  25                  30
Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
                100                 105                 110

Thr Phe Ala
        115

<210> SEQ ID NO 50
<211> LENGTH: 118
<212> TYPE: PRT
<213> ORGANISM: Homo sapiens
<220> FEATURE:
<221> NAME/KEY: SOURCE
<222> LOCATION: 1..118
<223> OTHER INFORMATION: /mol_type="protein"
      /note="D-DT; Accession No. NP_001346"
      /organism="Homo sapiens"

<400> SEQUENCE: 50

Met Pro Phe Leu Glu Leu Asp Thr Asn Leu Pro Ala Asn Arg Val Pro
1               5                   10                  15

Ala Gly Leu Glu Lys Arg Leu Cys Ala Ala Ala Ser Ile Leu Gly
                20                  25                  30

Lys Pro Ala Asp Arg Val Asn Val Thr Val Arg Pro Gly Leu Ala Met
        35                  40                  45

Ala Leu Ser Gly Ser Thr Glu Pro Cys Ala Gln Leu Ser Ile Ser Ser
    50                  55                  60

Ile Gly Val Val Gly Thr Ala Glu Asp Asn Arg Ser His Ser Ala His
65                  70                  75                  80

Phe Phe Glu Phe Leu Thr Lys Glu Leu Ala Leu Gly Gln Asp Arg Ile
                85                  90                  95

Leu Ile Arg Phe Phe Pro Leu Glu Ser Trp Gln Ile Gly Lys Ile Gly
                100                 105                 110

Thr Val Met Thr Phe Leu
        115
```